United States Patent
Wolf, II

(10) Patent No.: US 9,656,097 B2
(45) Date of Patent: *May 23, 2017

(54) APPARATUS AND METHOD USING NEAR INFRARED REFLECTOMETRY TO REDUCE THE EFFECT OF POSITIONAL CHANGES DURING SPINAL CORD STIMULATION

(71) Applicant: Erich W. Wolf, II, Lake Charles, LA (US)

(72) Inventor: Erich W. Wolf, II, Lake Charles, LA (US)

(*) Notice: Subject to any disclaimer, the term of this patent is extended or adjusted under 35 U.S.C. 154(b) by 665 days.

This patent is subject to a terminal disclaimer.

(21) Appl. No.: 14/019,240

(22) Filed: Sep. 5, 2013

(65) Prior Publication Data
US 2014/0005755 A1   Jan. 2, 2014

Related U.S. Application Data

(63) Continuation-in-part of application No. 13/780,470, filed on Feb. 28, 2013, now Pat. No. 9,132,273, which
(Continued)

(51) Int. Cl.
*A61N 1/36* (2006.01)
*A61N 5/06* (2006.01)
(Continued)

(52) U.S. Cl.
CPC .......... *A61N 5/0601* (2013.01); *A61B 5/1116* (2013.01); *A61N 1/0551* (2013.01);
(Continued)

(58) Field of Classification Search
CPC ................ A61N 5/0601; A61N 1/0551; A61N 1/36139; A61N 1/36071; A61B 5/1116
See application file for complete search history.

(56) References Cited

U.S. PATENT DOCUMENTS 5,076,270 A   12/1991   Stutz, Jr.
5,350,405 A * 9/1994   Silvian ................ A61N 1/3937
                                                          607/11
(Continued)

FOREIGN PATENT DOCUMENTS

WO   2007059362   5/2007

OTHER PUBLICATIONS

Philip, Geo M., et al., Fabrication of Negative Micro Axicons in Optical Fibers via Chemical Etching, ICOP 2009—International Conference on Optics and Photonics, Oct. 30, 2009, CSIO, Chandigarh, India.
(Continued)

*Primary Examiner* — George Evanisko
(74) *Attorney, Agent, or Firm* — Schultz & Assocaites, P.C.

(57) ABSTRACT

A positionally sensitive spinal cord stimulation apparatus and method using near-infrared (NIR) reflectometry are provided for automatic adjustments of spinal cord stimulation. The system comprises an electrode assembly with an integrated optical fiber sensor for sensing spinal cord position. The integrated optical fiber sensor, comprising a set of optical elements for emitting light from a set of IR emitters and for collecting reflected light into a set of IR photodetectors, determines a set of measured optical intensities. As the spinal cord changes position, the angles of incidence for light from the IR emitter and the measured optical intensities change. Electrode pulse characteristics are adjusted in real time, based on the set of measured optical intensities, to minimize changes in stimulation perceived by the patient during motion.

7 Claims, 21 Drawing Sheets

Related U.S. Application Data is a continuation-in-part of application No. 13/567,966, filed on Aug. 6, 2012, now Pat. No. 8,543,213, which is a continuation of application No. 12/925,231, filed on Oct. 14, 2010, now Pat. No. 8,239,038.

(60) Provisional application No. 61/867,413, filed on Aug. 19, 2013.

(51) Int. Cl.
    *A61B 5/11*      (2006.01)
    *A61N 1/05*      (2006.01)
    *A61B 5/00*      (2006.01)

(52) U.S. Cl.
CPC ..... *A61N 1/36071* (2013.01); *A61N 1/36139* (2013.01); *A61N 1/36157* (2013.01); *A61B 5/4836* (2013.01); *A61B 2562/0233* (2013.01); *A61N 1/36171* (2013.01); *A61N 1/36175* (2013.01)

(56) References Cited

U.S. PATENT DOCUMENTS

| | | | |
|---|---|---|---|
| 5,556,421 A | 9/1996 | Prutchi et al. | |
| 5,730,628 A | 3/1998 | Hawkins | |
| 5,824,021 A | 10/1998 | Rise | |
| 6,058,331 A | 5/2000 | King | |
| 6,120,467 A | 9/2000 | Schallhorn | |
| H1929 H * | 12/2000 | Citak | A61N 1/3706 607/28 |
| 6,169,924 B1 | 1/2001 | Meloy et al. | |
| 6,587,724 B2 * | 7/2003 | Mann | A61N 1/36164 607/30 |
| 6,622,048 B1 | 9/2003 | Mann et al. | |
| 6,871,099 B1 | 3/2005 | Whitehurst et al. | |
| 6,937,882 B2 | 8/2005 | Steuer et al. | |
| 7,127,296 B2 | 10/2006 | Bradley | |
| 7,162,304 B1 | 1/2007 | Bradley | |
| 7,216,000 B2 | 5/2007 | Sieracki et al. | |
| 7,263,402 B2 | 8/2007 | Thacker | |
| 7,330,762 B2 | 2/2008 | Boveja | |
| 7,333,857 B2 | 2/2008 | Campbell | |
| 7,359,751 B1 | 4/2008 | Erickson et al. | |
| 7,463,927 B1 | 12/2008 | Chaouat | |
| 7,539,543 B2 | 5/2009 | Schiff et al. | |
| 7,650,190 B2 | 1/2010 | Zhou et al. | |
| 7,684,869 B2 | 3/2010 | Bradley et al. | |
| 7,801,621 B1 * | 9/2010 | Thacker | A61B 5/6885 607/2 |
| 7,805,197 B2 | 9/2010 | Bradley | |
| 8,165,676 B2 * | 4/2012 | Donofrio | A61B 5/02028 600/301 |
| 2003/0065366 A1 * | 4/2003 | Merritt | A61N 1/3708 607/27 |
| 2003/0153959 A1 * | 8/2003 | Thacker | A61N 1/36071 607/48 |
| 2005/0096720 A1 * | 5/2005 | Sharma | A61B 5/042 607/122 |
| 2005/0222628 A1 | 10/2005 | Krakousky | |
| 2006/0217793 A1 * | 9/2006 | Costello | A61N 1/056 607/122 |
| 2007/0027514 A1 | 2/2007 | Gerber | |
| 2007/0100398 A1 | 5/2007 | Sloan | |
| 2007/0282403 A1 * | 12/2007 | Tearney | A61B 18/24 607/89 |
| 2008/0077190 A1 | 3/2008 | Kane et al. | |
| 2009/0118787 A1 | 5/2009 | Moffitt et al. | |
| 2009/0270960 A1 | 10/2009 | Zhao et al. | |
| 2010/0022861 A1 | 1/2010 | Cinbis et al. | |
| 2010/0105997 A1 | 4/2010 | Ecker et al. | |
| 2010/0106220 A1 | 4/2010 | Ecker et al. | |
| 2011/0029049 A1 * | 2/2011 | Vertikov | A61B 5/14532 607/104 |
| 2015/0306414 A1 | 10/2015 | Nielsen et al. | |

OTHER PUBLICATIONS

Utzinger, Urs, et al., Fiber Optic Probes for Biomedical Optical Spectroscopy, Feb. 2001, Tucson, Arizona.

Scott Prahl, Tabulated Molar Extinction Coefficient for Hemoglobin in Water, http://omlc.ogi.edu/spectra/hemoglobin/summary.html, Mar. 4, 1998, pp. 1-7.

Urs Utzinger, Oxygen saturation, http://www2.engr.arizona.edu/~bme517/supporting%20documents/PulseOximeter/Pulse%20Oxi%20Meter%20Laboratory.htm#_Toc67647950, 2002, pp. 1-24.

* cited by examiner

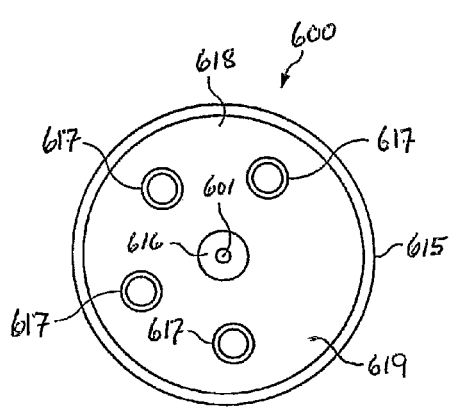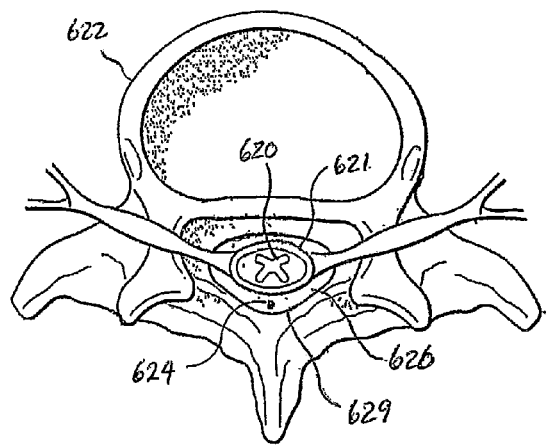
FIG. 6c
FIG. 6d

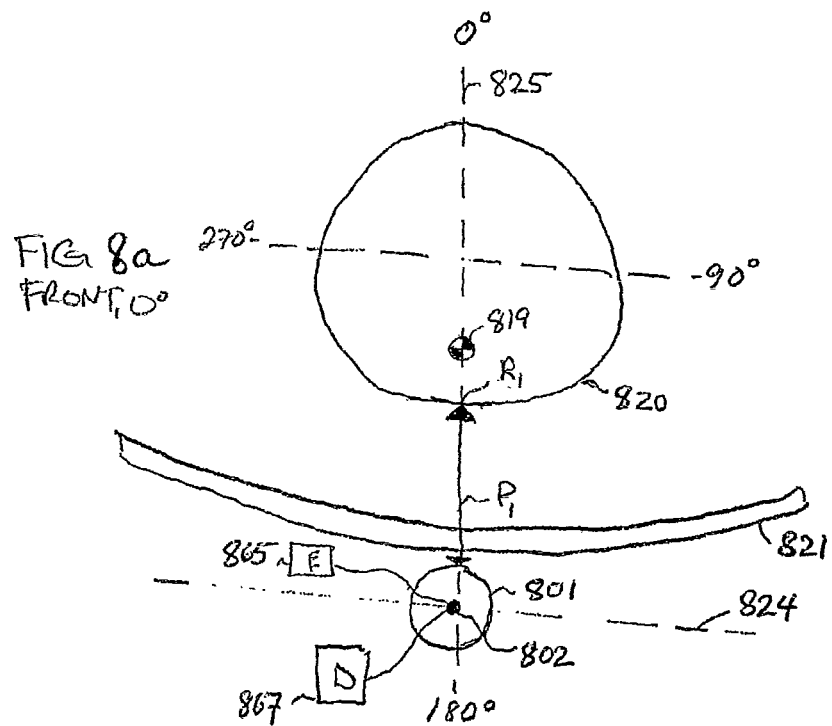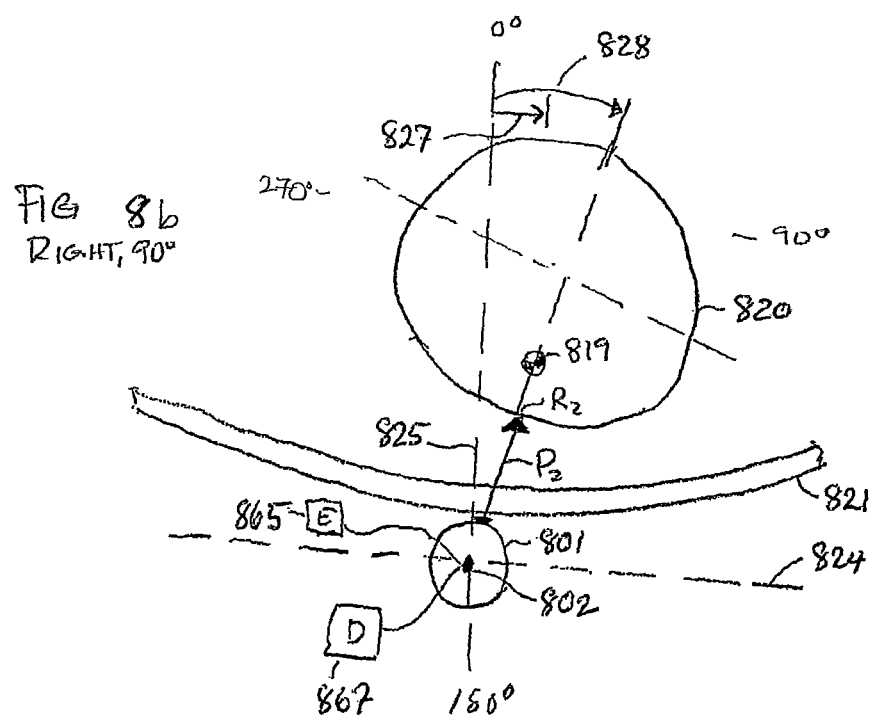

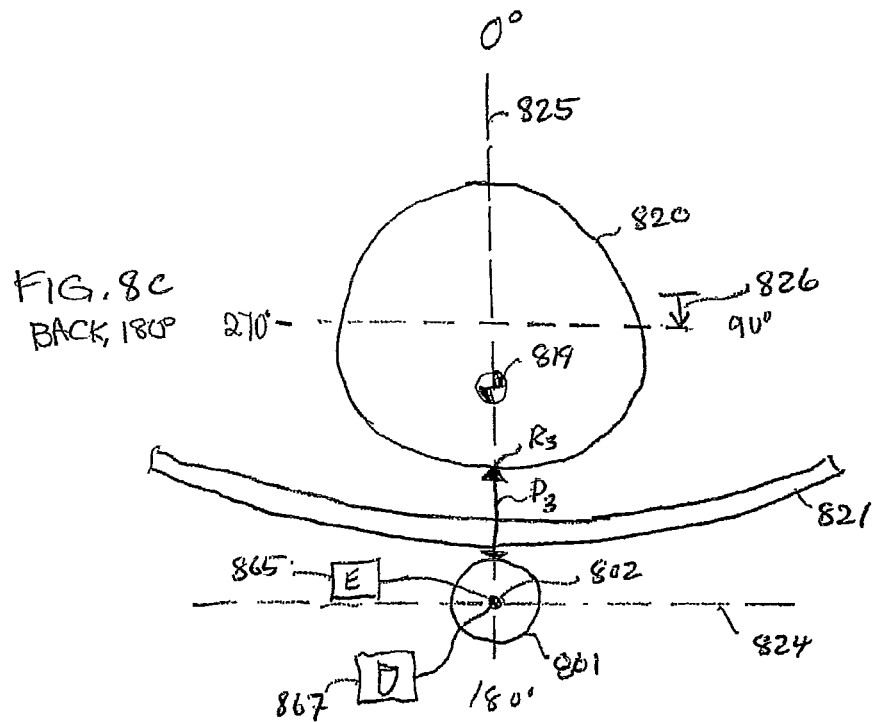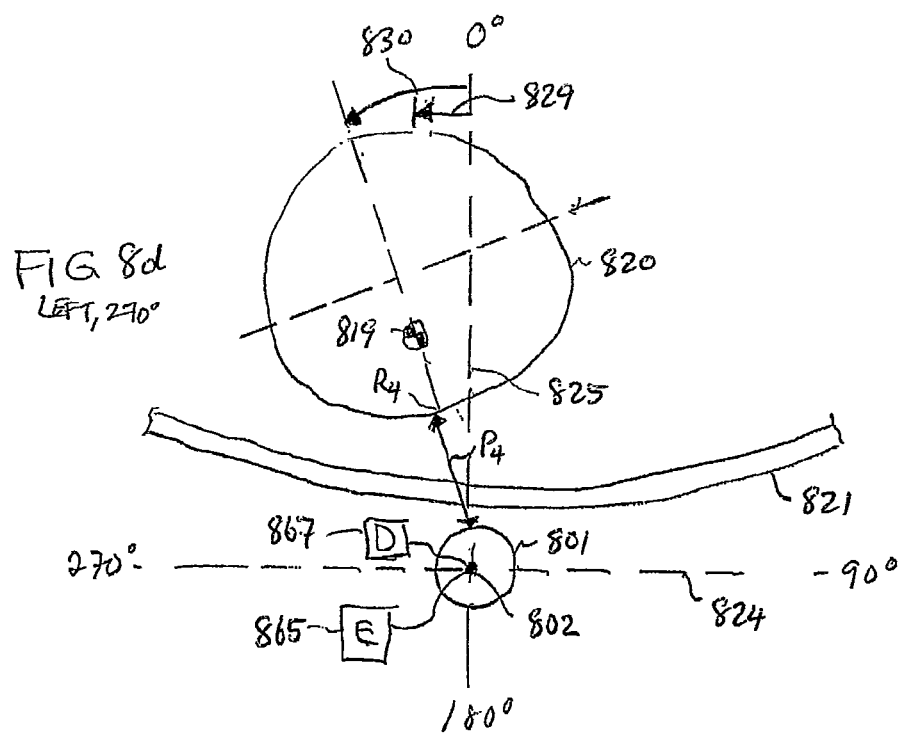

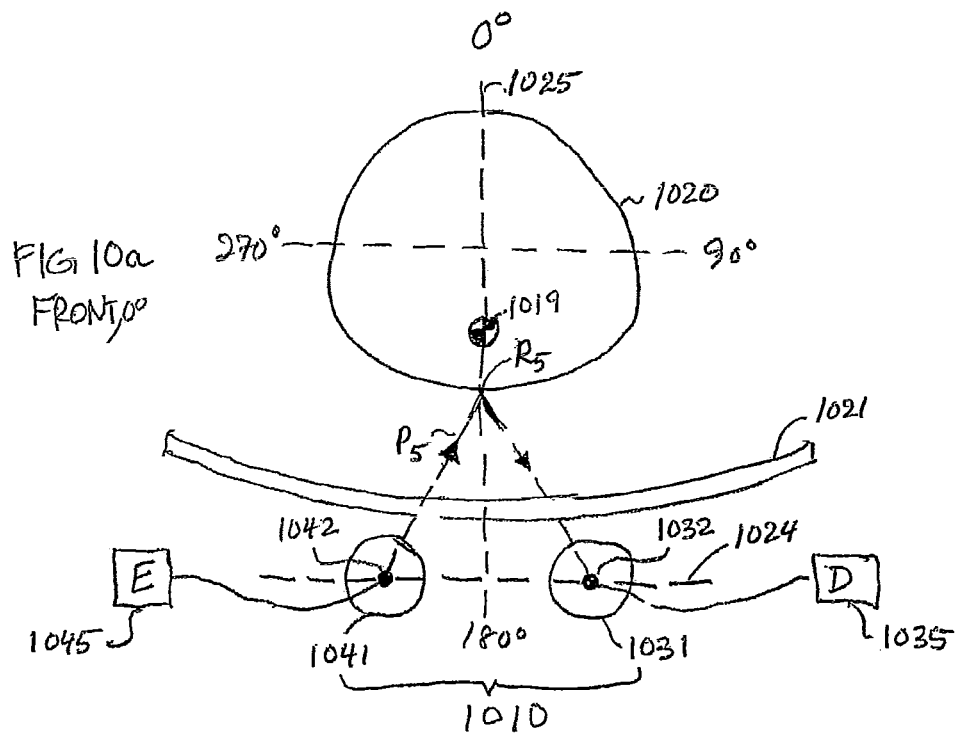
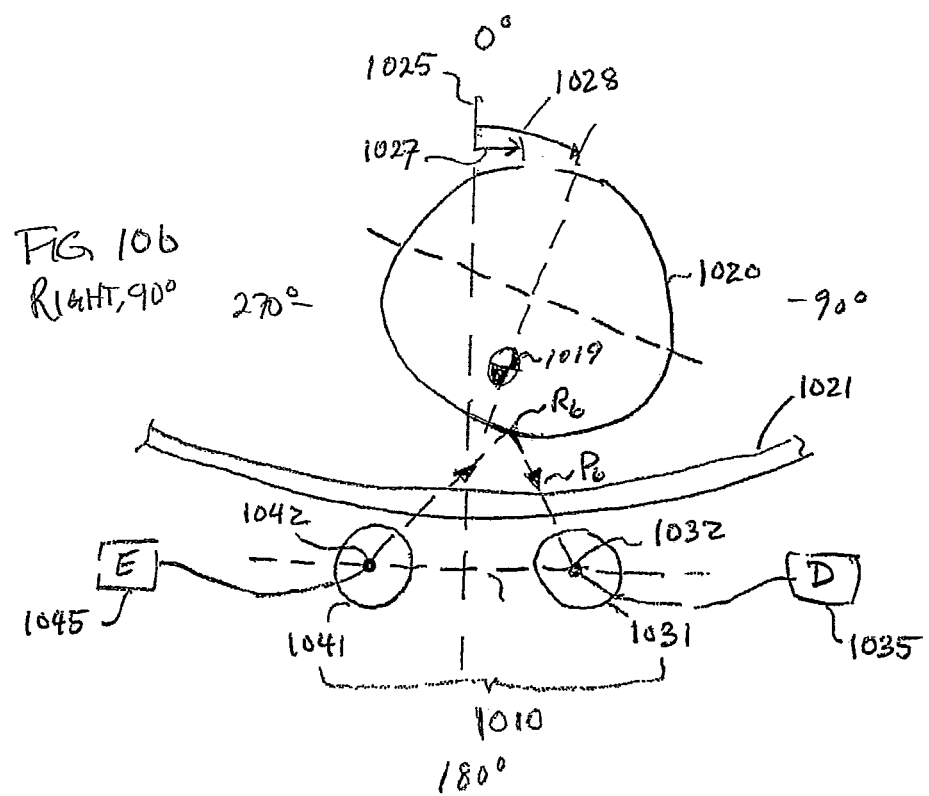

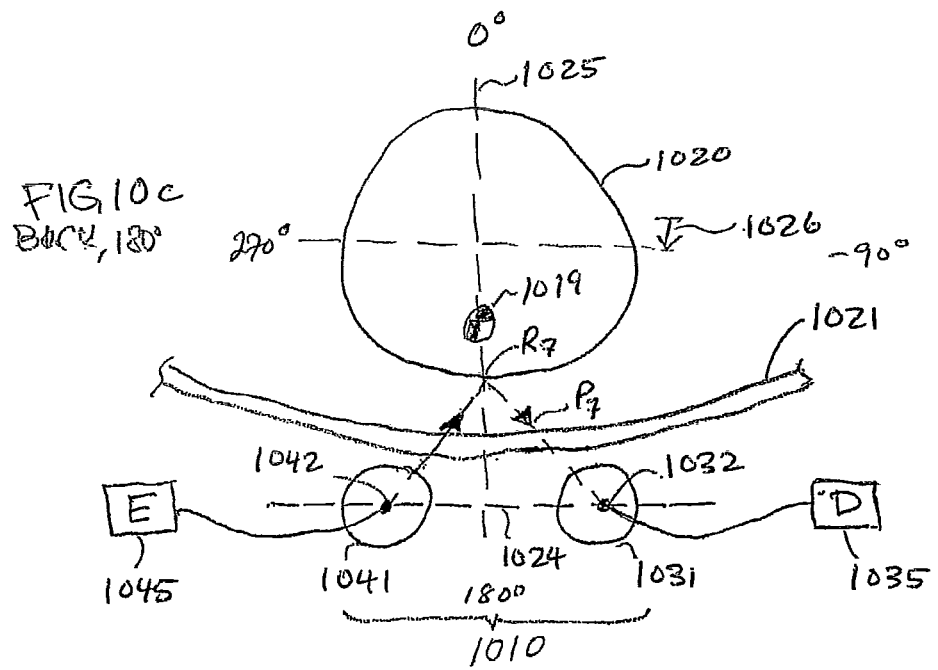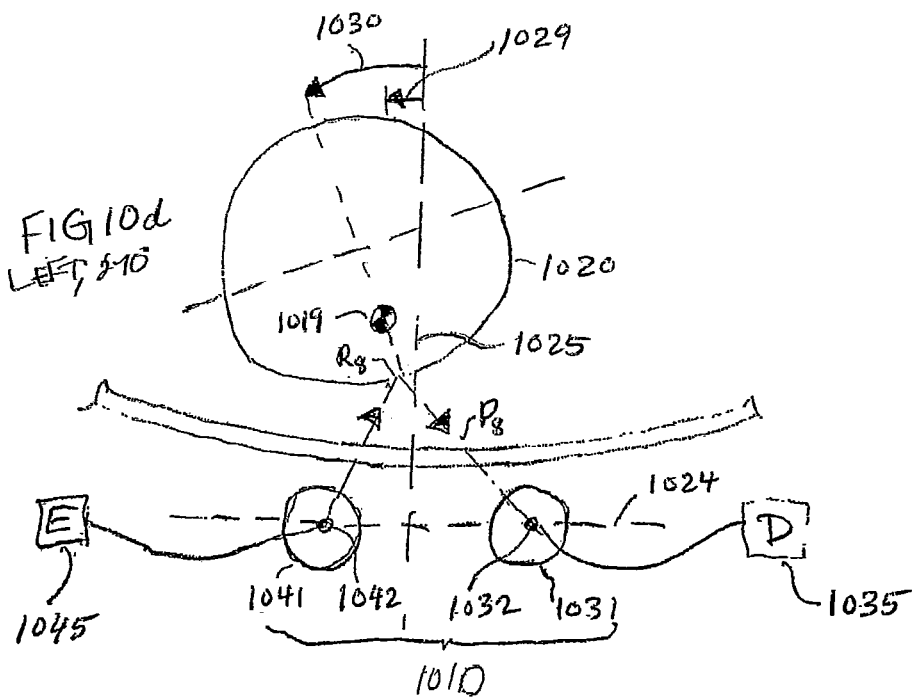

| patient position | Photo-detector PD | Pulse amplitude | Pulse width | Pulse frequency |
|---|---|---|---|---|
| 1. (forward) - 0° | $PD_1$ | $A_1$ | $PW_1$ | $PF_1$ |
| 2. (right) - 90° | $PD_2$ | $A_2$ | $PW_2$ | $PF_2$ |
| 3. (left) – 270° | $PD_3$ | $A_3$ | $PW_3$ | $PF_3$ |
| 4. (back) - 180° | $PD_4$ | $A_4$ | $PW_4$ | $PF_4$ |

FIG. 19

| patient position | Photo-detector PD | Left Pulse amplitude | Right Pulse amplitude | Pulse width | Pulse frequency |
|---|---|---|---|---|---|
| 1. (forward) - 0° | $PD_1$ | $A_{L1}$ | $A_{R1}$ | $PW_1$ | $PF_1$ |
| 2. (right) - 90° | $PD_2$ | $A_{L2}$ | $A_{R2}$ | $PW_2$ | $PF_2$ |
| 3. (left) – 270° | $PD_3$ | $A_{L3}$ | $A_{R3}$ | $PW_3$ | $PF_3$ |
| 4. (back) - 180° | $PD_4$ | $A_{L4}$ | $A_{R4}$ | $PW_4$ | $PF_4$ |

FIG. 20

APPARATUS AND METHOD USING NEAR INFRARED REFLECTOMETRY TO REDUCE THE EFFECT OF POSITIONAL CHANGES DURING SPINAL CORD STIMULATION

CROSS-REFERENCE TO RELATED APPLICATIONS

This application is a Continuation-in-Part Application of U.S. patent application Ser. No. 13/780,470, filed Feb. 28, 2013, which is a Continuation-in-Part Application of U.S. patent application Ser. No. 13/567,966, filed Aug. 6, 2012, which is continuation of U.S. patent application Ser. No. 12/925,231, filed Oct. 14, 2010, now U.S. Pat. No. 8,239,038. This application claims priority to U.S. Provisional Patent Application No. 61/867,413, filed Aug. 19, 2013. Each patent application identified above is incorporated here by reference in its entirety to provide continuity of disclosure.

FIELD OF INVENTION

This invention relates generally to spinal cord stimulation (SCS) and technique for automatic adjustments of SCS using near-infrared (NIR) reflectometry.

BACKGROUND

Spinal cord stimulation is a technique which uses an implanted electrode array to control chronic pain. The electrode array is typically implanted in a fixed position within the epidural space near the spinal cord. A signal generator delivers current pulses to the spinal cord via the implanted electrode array. The current pulses induce parasthesias which help block the perception of pain.

In FIG. 1, spinal column 1 is shown to have a number of vertebrae, categorized into four sections or types: lumbar vertebrae 2, thoracic vertebrae 3, cervical vertebrae 4 and sacral vertebrae 5. Cervical vertebrae 4 include the 1st cervical vertebra (C1) through the 7th cervical vertebra (C7). Just below the 7th cervical vertebra is the first of twelve thoracic vertebrae 3 including the 1st thoracic vertebra (T1) through the 12th thoracic vertebra (T12). Just below the 12th thoracic vertebrae 3, are five lumbar vertebrae 2 including the 1st lumbar vertebra (L1) through the 5th lumbar vertebra (L5), the 5th lumbar vertebra being attached to sacral vertebrae 5 (S1 to S5), sacral vertebrae 5 being naturally fused together in the adult.

In FIG. 2, representative vertebra 10, a thoracic vertebra, is shown to have a number of notable features which are in general shared with lumbar vertebrae 2 and cervical vertebrae 4. The thick oval segment of bone forming the anterior aspect of vertebra 10 is vertebral body 12. Vertebral body 12 is attached to bony vertebral arch 13 through which spinal nerves 11 run. Vertebral arch 13, forming the posterior of vertebra 10, is comprised of two pedicles 14, which are short stout processes that extend from the sides of vertebral body 12 and bilateral laminae 15. The broad flat plates that project from pedicles 14 join in a triangle to form a hollow archway, spinal canal 16. Spinous process 17 protrudes from the junction of bilateral laminae 15. Transverse processes 18 project from the junction of pedicles 14 and bilateral laminae 15. The structures of the vertebral arch protect spinal cord 20 and spinal nerves 11 that run through the spinal canal.

Surrounding spinal cord 20 is dura 21 that contains cerebrospinal fluid (CSF) 22. Epidural space 24 is the space within the spinal canal lying outside the dura.

Referring to FIGS. 1, 2 and 3, the placement of an electrode array for spinal cord stimulation according to the prior art is shown. Electrode array 30 is positioned in epidural space 24 between dura 21 and the walls of spinal canal 16 towards the dorsal aspect of the spinal canal nearest bilateral laminae 15 and spinous process 17.

FIG. 4 shows a prior art electrode array 30 including a set of electrode contacts 35 sealed into elastomeric housing 36. Electrode array 30 has a set of electrode leads 31 which are connected to electrical pulse generator 32 and controller 33. The electrical pulse generator may be outside of the body or it may be implanted subcutaneously. Each electrode contact has a separate electrical conductor in the set of electrode leads 31 so that the current to each contact may be independently conducted and controlled.

The anatomical distribution of parasthesias is dependent upon the spatial relationship between a stimulating electric field generated by the electrode array and the neuronal pathways within the spinal cord. The distribution may be changed by altering the current across one or more electrodes of the electrode array. Changing anode and cathode configurations of the electrode array also alters the distribution and hence, the anatomical pattern of the induced parasthesias.

Proper intensity of the current pulses is important. Excessive current produces an uncomfortable sensation. Insufficient current produces inadequate pain relief. Body motion, particularly bending and twisting, causes undesired and uncomfortable changes in stimulation due to motion of the spinal cord relative to the implanted electrode array.

There are methods and systems for controlling implanted devices within the human body. For example, Ecker et al, in U.S. Patent Application No. 2010/0105997, discloses an implantable medical device that includes a controller and a plurality of sensor modules. A sensor includes at least one light source that emits light at a particular wavelength, which scatters through blood-perfused tissue a detector senses the light reflected by blood mass of a patient.

U.S. Pat. No. 7,684,869 to Bradley, et al. discloses a system using an interelectrode impedance to determine the relative orientation of a lead with respect to other leads in the spinal column. Bradley et al. further disclose that interelectrode impedance may be used to adjust stimulation energy.

U.S. Patent Publication No. 2009/0118787 to Moffitt, et al. discloses electrical energy conveyed between electrodes to create a stimulation region. Physiological information from the patient is acquired and analyzed to locate a locus of the stimulation region. The stimulation region is electronically displaced.

Deficiencies exist in the prior art related to accuracy of spinal cord stimulation in relieving pain under changing circumstances. The deficiencies are most pronounced while the patient is moving. The prior art does not provide a satisfactory way to automatically adjust spinal cord stimulation to compensate for motion between the electrodes and the spinal cord to maintain a constant level of pain relief during patient motion.

SUMMARY OF PREFERRED EMBODIMENTS

Embodiments of the present invention operate to automatically adjust spinal cord stimulation to compensate for patient movement. Automatic adjustment results in consistent parasthesias and conservation of battery power.

The disclosure demonstrates a novel optical sensor, generally useful in many fields of endeavor, in which a probe light beam is emitted from the sensor and a responsive light beam is collected by the sensor, where the sensor comprises a negative axicon element coupled to an optical fiber. In a preferred embodiment, the negative axicon is embedded in the end of the optical fiber. The optical fiber is further coupled to an active optical element which can be an optical emitter or an optical detector.

Disclosed is a stimulator system having a stimulator lead encasing the optical fiber, a controller, an optical emitter operatively connected to the controller generating an emitted light beam into the optical fiber. An optical detector operatively connected to the controller, receives a set of reflected light beams from the optical fiber. A set of electrodes are operatively connected to the controller and the controller directs a set of currents to the set of electrodes based on the set of reflected light beams.

In a preferred embodiment of the stimulator system having two stimulator leads, the first stimulator lead encases an optical fiber coupled to an optical emitter and an optical element for emitting light into an epidural space. The second stimulator lead encases an optical fiber coupled to an optical detector and an optical element for collecting and detecting light from an epidural space. Both leads have a set of electrodes.

In another embodiment of the stimulator system, a single stimulator lead encases an optical fiber which is coupled to an optical emitter and further coupled to an optical detector in the set of optical detectors. An optical circulator is operatively coupled to the optical emitter, the optical detector and the optical fiber.

In an aspect of the system, the stimulator lead is an implantable lead encasing the optical fiber in a lumen wherein the implantable lead further comprises an EMI shield. In a related aspect, the implantable lead further comprises carbon nanotubes.

In another aspect of the system, the controller derives a set of current amplitudes for the set of currents based on an interpolation of a set of calibrated current amplitudes.

In another aspect of the system, the controller derives a set of current amplitudes based on time averaging of a set of historical current amplitudes.

In yet another aspect of the system, the controller derives a current pulse width for the set of currents based on at least one of the group consisting of time averaging a set of current pulse widths, time averaging a set of current amplitudes, interpolating the set of current pulse widths and interpolating the set of current amplitudes.

In yet another aspect of the system, the controller derives a set of current pulse frequencies for the set of currents based on at least one of the group consisting of time averaging a set of current pulse frequencies, time averaging a set of current amplitudes, interpolating the set of current pulse frequencies and interpolating the set of current amplitudes.

In a preferred embodiment, the system further comprises a calibration and programming unit operatively connected to the controller for calibrating the set of current pulse amplitudes, pulse widths and pulse frequencies.

BRIEF DESCRIPTION OF DRAWINGS

The following disclosure is understood best in association with the accompanying figures. Like components share like numbers.

FIG. 6c shows a cross-section of a stimulator lead along line 6c-6c from FIG. 6a.

FIG. 6d shows placement of a set of stimulator leads.

FIG. 8a shows a cross-sectional view of a single stimulator lead embodiment with a spinal cord at a forward position with respect to a stimulator lead.

FIG. 8b shows a cross-sectional view of a single stimulator lead embodiment with a spinal cord at a rightward position with respect to a stimulator lead.

FIG. 8c shows a cross-sectional view of a single stimulator lead embodiment with a spinal cord at posterior position with respect to a stimulator lead.

FIG. 8d shows a cross-sectional view of a single stimulator lead embodiment with a spinal cord at leftward position with respect to a stimulator lead.

FIG. 10a shows a cross-sectional view of a dual stimulator lead embodiment with two optical elements located in relation to a spinal cord at a forward position.

FIG. 10b shows a cross-sectional view of a dual stimulator lead embodiment with two optical elements located in relation to a spinal cord at a rightward position.

FIG. 10c shows a cross-sectional view of a dual stimulator lead embodiment with two optical elements located in relation to a spinal cord at a backward position.

FIG. 10d shows a cross-sectional view of a dual stimulator lead embodiment with two optical elements located in relation to a spinal cord at a leftward position.

FIG. 19 is a graphic representation of a calibration table for a single lead system with one optical emitter, one optical detector and a set of electrodes.

FIG. 20 is a graphic representation of a calibration table for a dual lead system with one optical emitter, one optical detector and a set of electrodes.

DETAILED DESCRIPTION

Figures 1, 4:
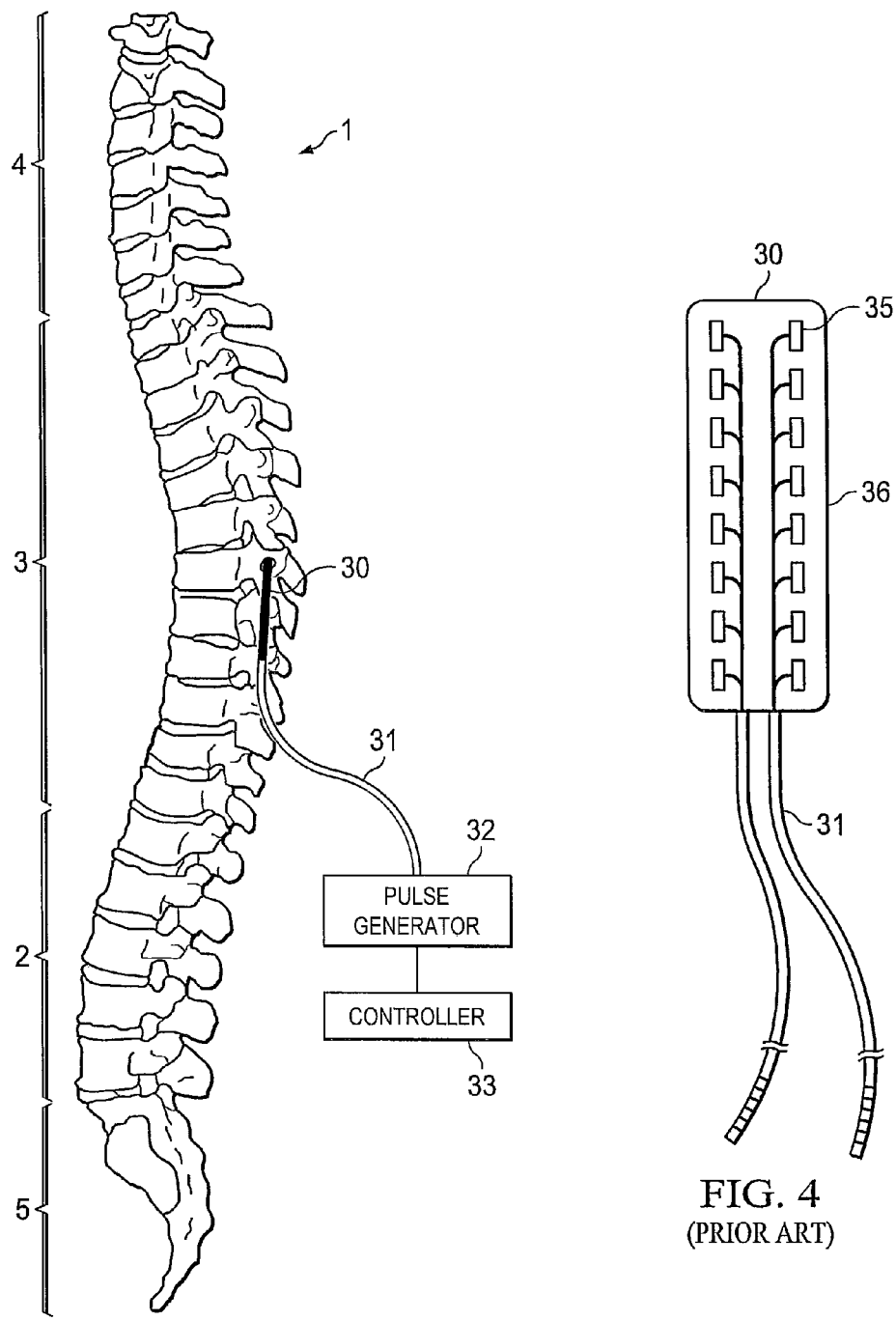
FIG. 1 shows a view of the human spine showing the various types of vertebrae and an approximate position of an electrode array for spinal cord stimulation.
FIG. 4 shows a prior art electrode array for spinal cord stimulation.
Figure 2:
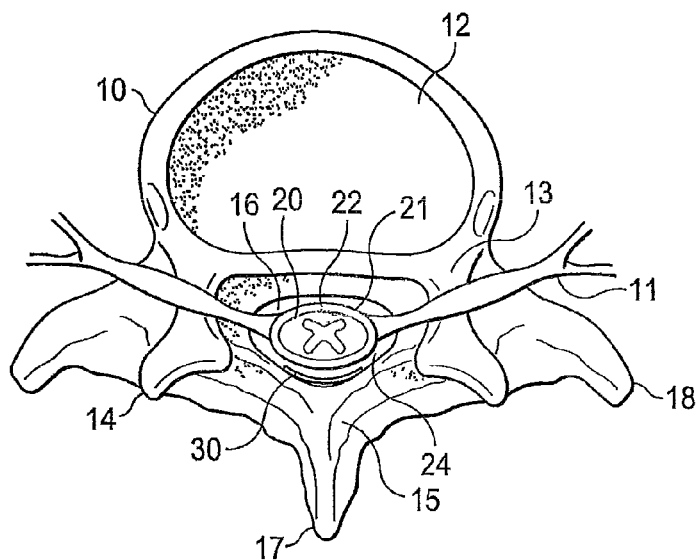
FIG. 2 shows an axial view of a thoracic vertebra indicating the position of the spinal cord and an electrode array for spinal cord stimulation.
Figure 3:
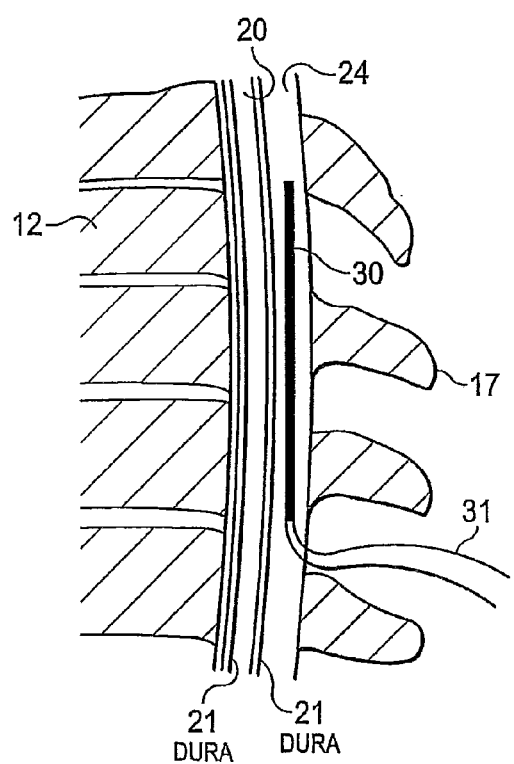
FIG. 3 shows a sagital cross section view of the human spine showing the approximate position of an electrode array for spinal cord stimulation.

The distance between a stimulating electrode and the spinal cord surface may be inferred from a function dependent upon: 1) the optical path lengths of light between a near infrared light emitter and a set of optical detectors, where the light is reflected from the spinal cord; 2) the spinal cord geometry; 3) the optical divergence of the light emitter; and 4) the presence of chromophores in the optical path.

The dura surrounding the spinal cord itself is translucent to near infrared light. Near infrared light will be scattered by, and will reflect from, the spinal cord. Cerebrospinal fluid (CSF) will negligibly scatter near infrared light and will not act as a significant reflector of near-infrared light. Light from the light emitter passes through the thin, relatively avascular dura to enter the CSF. Light incident on the spinal cord experiences scatter resulting in a portion being reflected and another portion being absorbed by chromophores.

Optical absorption in a fluid medium may be described by the Beer-Lambert Law (Beer's Law), which is reasonably accurate for a range of chromophores and concentrations. Beer's Law states that the optical absorbance of a fluid with a chromophore concentration varies linearly with path length through the fluid and the chromophore concentration as:

$$A_\lambda = \epsilon_\lambda bc, \quad\quad\quad (\text{Eq. 1})$$

where:

$\epsilon_\lambda$=molar absorptivity or extinction coefficient of the chromophore at wavelength $\lambda$ (the optical density of a 1-cm thick sample of a 1 M solution);

b=sample path length in centimeters; and, c=concentration of the compound in the sample, in molarity (mol L$^{-1}$).

The absorbance ($A_\lambda$) at a wavelength $\lambda$ is related to the ratio of light energy passing through the fluid, I, to the incident light energy, $I_0$, in $$A_\lambda = -\log(I/I_0). \quad\quad\quad (\text{Eq. 2})$$

For deoxyhemoglobin and oxyhemoglobin, the extinction coefficient spectra are well known.

The path length within the spinal cord is dependent upon the geometry of the ellipsoid shaped spinal cord and its normal vector relative to the optical axes of the emitter and detector pair.

The optical path length within CSF is roughly equal to the nominal geometric path length as the scatter is small and the index of refraction does not vary considerably along the path. Light absorption of the CSF may be approximated by that of its primary constituent, $H_2O$. Sensitivity of the system to CSF path length may be optimized using a light wavelength at a local maxima of the water extinction coefficient curve near 950-1100 nm.

When considering the light emitter wavelength, one must also consider the extinction coefficients of the primary chromophores, deoxy- and oxy-hemoglobin. To minimize effects of blood flow changes within the spinal cord (although these are thought to be insignificant in the quasi-static sense), one may select the isosbestic wavelength of these chromophore species, preferably at about 805 nm.

The geometry of the light emitter and detector aperture relative to the spinal cord is the parameter most prone to variability. The variance results from factors such as dependence upon placement of the electrode within the spinal canal, canal diameter, spinal cord shape, spinal cord caliber, and presence of scoliotic or kyphotic curvature within the spine. Consequently, this geometric parameter is the primary reason that the system must be calibrated, in situ, in vivo. Spinal cord position may then be inferred through various methods from data obtained at ordinal body positions.

The effects of geometry may be minimized by minimizing the angle between the light emitter and optical detector optical axes relative to the spinal cord surface normal vector.

The beam divergence of the light emitter relative to the incident and reflected rays will influence the detected light amplitude.

It is desirable to maintain a constant electric field at a group of target cells in the spinal cord as the spinal cord moves in order to consistently reduce the transmission of a pain sensation to the brain. With the patient in a prone position or bending forward (0° direction), the spinal cord moves anterior within its orbit in the spinal canal. An equal increase in stimulation pulse amplitude for each electrode pair is required to maintain the same electric field density. In the right lateral position or bent to the right (90° direction), the spinal cord moves to the right within its orbit in the spinal canal. A decrease in electrode stimulation pulse amplitude in the right electrode and an increase in electrode stimulation pulse amplitude in the left electrode of the electrode pair is required. In the supine position or bending backward (180° direction), the spinal cord moves dorsally within its orbit within the spinal canal. A decrease in electrode stimulation pulse amplitude bilaterally is required to maintain a constant electric field across the spinal cord. In the left lateral position or bent toward the left (270° direction), the spinal cord moves to the left within its orbit. A decrease in electrode stimulation pulse amplitude in the left electrode and an increase in electrode stimulation pulse amplitude in the right electrode of the electrode pair is required.

Figure 5:
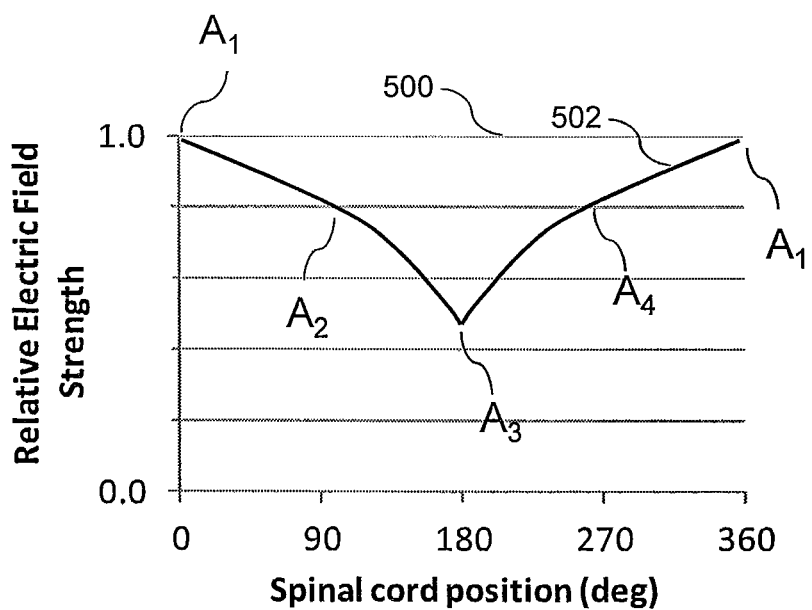
FIG. 5 shows the relative electric field produced by a preferred embodiment for the spinal cord in various positions within the spinal canal.

FIG. 5 shows a plot 500 of relative electric field strength 502 required to be generated at a the electrodes, respectively, for maintenance of a constant field at any point across in a horizontal cross section of the spinal cord as the spinal cord is moved through an orbit of 360° in the spinal canal. The electric field strength at points $A_1$-$A_4$ will be described in more detail below in relation to electrode current amplitude.

Figure 6A:
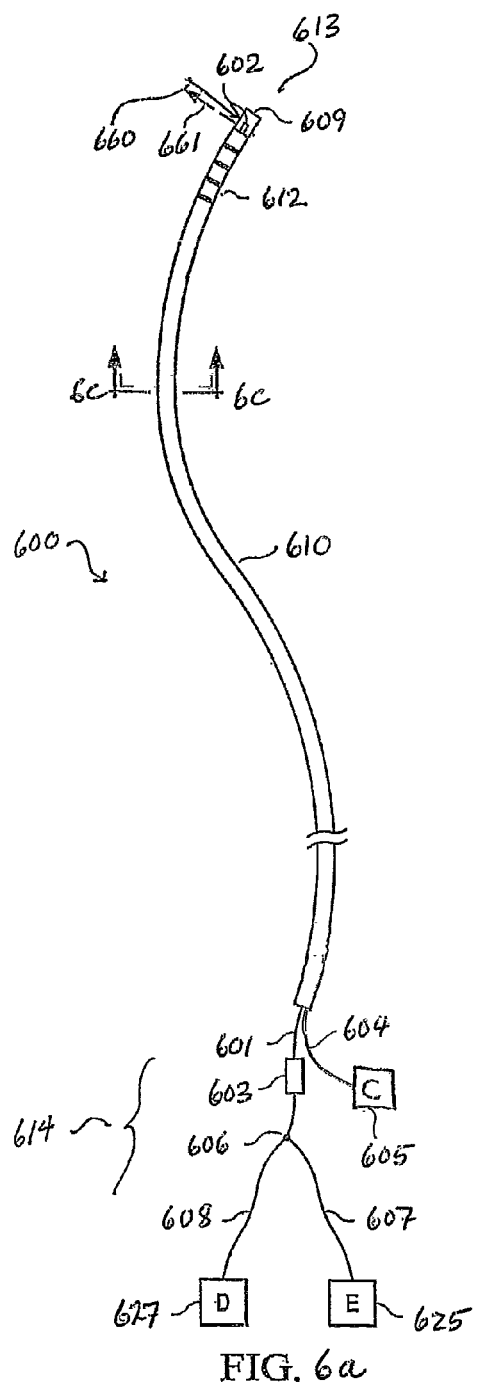
FIGS. 6a-6b shows two perspective views of a stimulator lead for spinal cord stimulation incorporating an optical fiber.
Figure 6B:
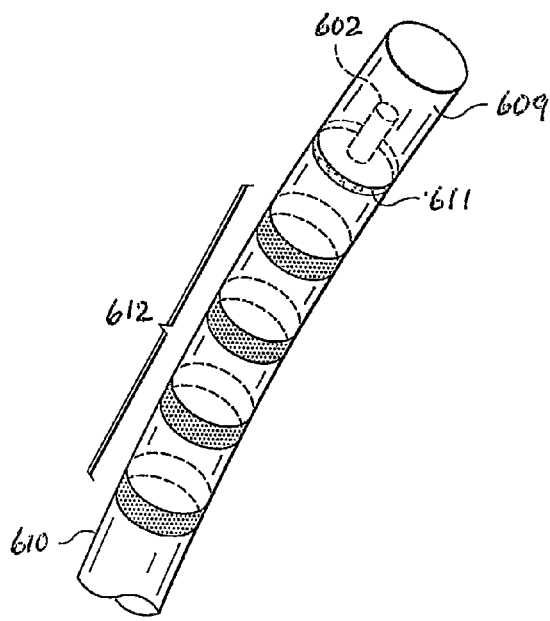

Referring to FIGS. 6a and 6b, a preferred embodiment of a percutaneous stimulator lead is shown. Stimulator lead 600 includes lead cable 610 housing optical fiber 601 which is coupled to distal optical element 602 at a distal end 613 and coupled to optical fiber connector 603 at a proximal end 614. Optical fiber connector 603 is further coupled to optical circulator 606. Optical circulator 606 is connected to optical fiber 607 which is further coupled to optical emitter 625. Optical circulator 606 is also connected to optical fiber 608 which is further coupled to optical detector 627. Distal optical element 602 is configured as both an optical emitter and an optical collector. A set of electrodes 612, near the distal end, is coupled to a current source 605 through a set of electrical leads 604 also housed in lead cable 610.

A suitable optical circulator is the PIOC310P component from AC Photonics, Inc., of Santa Clara, Calif., operating at a wavelength of 1060 nm Optical circulators of smaller size and operating at wavelengths longer than 1060 nm are also suited for these embodiments. Optical circulators of larger size and operating at wavelengths shorter than 1060 nm are also suited for these embodiments.

Distal optical element 602 extends into cap 609. In a preferred embodiment, cap 609 is an extension of lead cable 610 which is sealed at the distal tip and bonded to lead cable 610 with adhesive at 611. Cap 609 is a NIR-transparent hollow cylinder preferably comprised of glass or plastic and may contain an index matching fluid.

In another embodiment, cap 609 is comprised of a solid cylinder formed in place around distal optical element 602. In this embodiment, the cylinder is not hollow and is comprised of a transparent plastic such as Lexan™. In another embodiment, cap 609 is a continuation of the lead cable 610 which may be constructed of polyurethane or other suitable material and is sealed at the distal tip.

Referring to FIG. 6c, a cross-section of stimulator lead 600 is shown. Stimulator lead 600 includes sheathed outer surface 615 which encapsulates a set of electrode leads 617, lumen 616 in filler material 619. Lumen 616 encloses optical fiber 601. Lumen 616 also provides a hollow cavity for a wire stylet to be inserted into the lead cable for the purpose of directing the position of the lead cable while being inserted into the epidural space of a patient. Optical fiber 601 is inserted after removing the wire stylet from lumen 616.

In an alternate embodiment an additional lumen is included in the stimulator lead to provide a separate cavity for the wire stylet.

In a preferred embodiment, sheathed outer surface 615 includes an EMI shield. Filler material 619 preferably includes a polyimide polymer. Filler material 619 can also include additional materials with physical properties that enhance the EMI shielding capability of lead cable 610.

In an alternate embodiment, filler material 619 may include a carbon nano-tube composite such as that disclosed in U.S. Pat. No. 7,413,474 to Liu, et al. The disclosure of U.S. Pat. No. 7,413,474 is incorporated herein by reference.

Referring to FIG. 6d, where a vertebra 622 encloses a spinal cord 620, a single stimulator lead 624 is placed in the epidural space 626 of vertebra 622 between the dura 621 and the walls of the spinal canal 629. In a preferred single lead embodiment, stimulator lead 624 is configured with at least one optical fiber and with both an optical emitter and optical collector. Additional embodiments of a single stimulator lead system are possible which include multiple optical fibers in a single-lead assembly.

Referring again to FIG. 6a, in use, probe light beam 661 is emitted from optical emitter 625 and propagates through first optical fiber 607, through optical fiber 601, and exits from optical element 602. A responsive light beam 660 is collected by optical element 602 and propagates through optical fiber 601, through second optical fiber 608 and detected by optical detector 627. Optical circulator 606 allows responsive light beam 660 to propagate into second optical fiber 608 but not into first optical fiber 607. Optical circulator 606 also allows probe light beam 661 to propagate into optical fiber 601 but not into second optical fiber 608.

Responsive light beam 660 is generated through interaction between probe light beam 661 and tissue within the spinal canal. For example, probe light beam propagates through spinal canal, experiences absorption, is reflected by components within the spinal canal, and then experiences additional absorption before being collected as a responsive light beam with a different intensity and a different spectral profile.

FIGS. 7a-7g show suitable optical configurations for an optical element disposed on an optical fiber at the distal end of a stimulator lead. FIGS. 7a-7g are intended as examples and should not be interpreted as limiting to the invention.

Figure 7A:
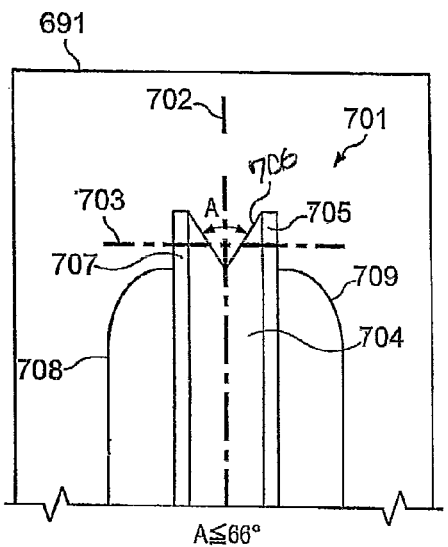
FIGS. 7a-7g show various embodiments of a distal optical element.

In FIG. 7a, distal optical element 701 includes optical fiber 708 encased in cap 691. Optical fiber 708 includes optical axis 702 having core 704 surrounded by cladding 705 further surrounded by jacket 709. Optical fiber 701 further includes negative axicon 706 etched at the distal end, centered on optical axis 702, and having an angular extent A. Angular extent A is less than about 66° for typical glass. The maximum value of A is determined as twice the complement of the critical angle α for the optical material in core 704. The complement of the critical angle is (90°−α). Jacket 709 is removed from optical fiber 708 for a distance 707 approximately the same as the depth of negative axicon 706. When light travels through optical fiber 708 and out of the distal end, it will be emitted approximately perpendicular to the optical axis 702 near lateral line 703 in a radially symmetric 360 degree pattern. When used as an optical collector, optical fiber 708 will collect light through a 360 degree angle from directions near lateral line 703.

Figure 7B:
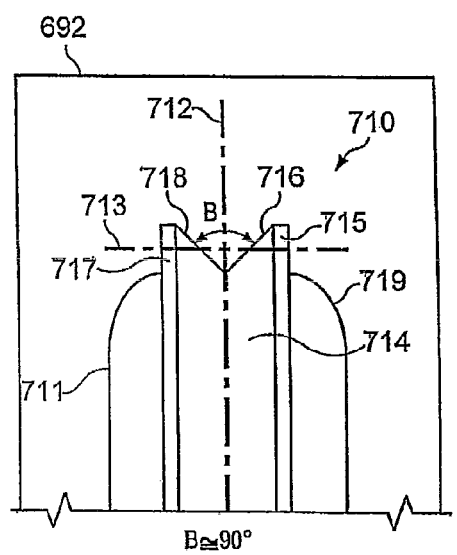

In FIG. 7b, distal optical element 710 comprises an optical fiber 711 covered by cap 692. Optical fiber 710 includes optical axis 712 having core 714 surrounded by cladding 715 which is further surrounded by jacket 719. Optical fiber 711 includes negative axicon 716 etched at the distal end, centered on optical axis 712, and having an angular extent B. Angular extent B is approximately 90°. Jacket 719 is removed from optical fiber 711 for a distance 717 approximately the same as the depth of negative axicon 716. Outer surface of negative axicon 716 is coated with a reflective coating 718. When light travels through optical fiber 711 and out of the distal end, it will be emitted approximately perpendicular to the optical axis 712 near lateral line 713 in a uniform 360 degree pattern. When used as an optical collector, optical fiber 711 will collect light from through a 360 degree angle from directions near the lateral line 713.

A negative axicon can be fabricated in an optical fiber end by a chemical etching process using about a 50% solution of hydrofluoric acid with a buffer of $NH_4F$ in deionized water. Volume ratio of HF to buffer is varied to achieve varying negative axicon angles.

Figure 7G:
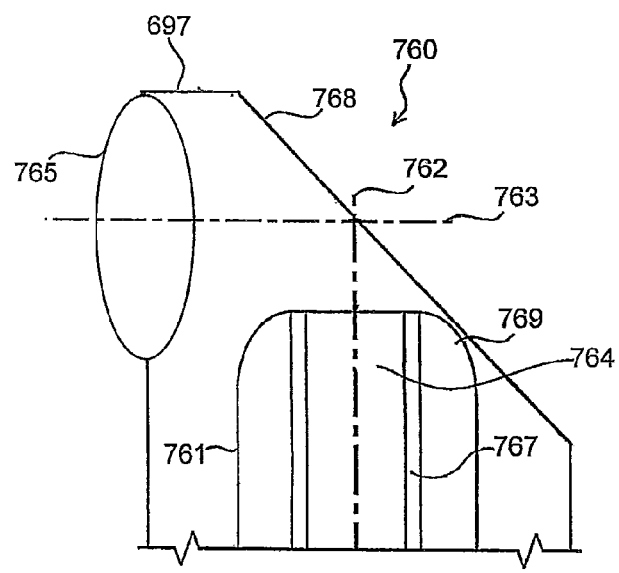
Figure 7C:
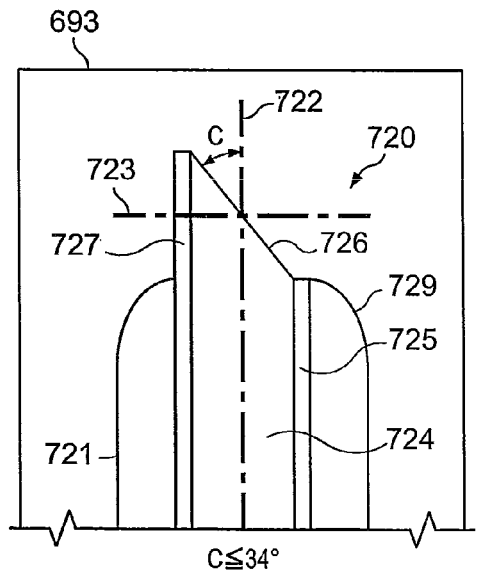

In FIG. 7c, distal optical element 720 is enclosed in cap 693 and comprises optical fiber 721. Optical fiber 721 includes optical axis 722 having core 724 surrounded by cladding 725 which is further surrounded by jacket 729. Optical fiber 721 includes beveled surface 726 etched at the distal end at an angle C. Angle C is less than about 34° for typical glass. The value of C is determined as the complement of the critical angle for the optical material in core 724. Jacket 729 is removed from optical fiber 721 for a distance 727 approximately the same as the depth of beveled surface 726. When light travels through optical fiber 721 and out of the distal end, it will be emitted approximately perpendicular to the optical axis 722 near lateral line 723 in an angular pattern determined by the position of the beveled surface. When used as an optical collector, optical fiber 721 will collect light in the approximate angular pattern from horizontal directions near the lateral line 723.

Figure 7D:
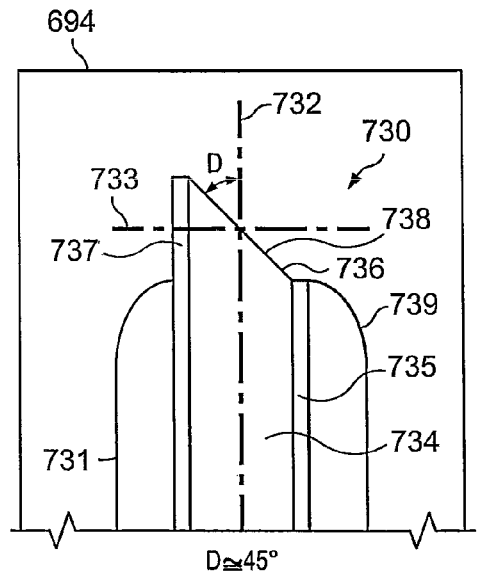

In FIG. 7d, distal optical element 730 is encased in transparent cap 694 and comprises optical fiber 731. Optical fiber 731 includes optical axis 732 having core 734 surrounded by cladding 735 which is further surrounded by jacket 739. Optical fiber 731 includes a beveled surface 736 etched at the distal end at an angle D where D is about 45°.

Beveled surface 736 has a reflective coating 738. Jacket 739 is removed from optical fiber 731 for a distance 737 approximately the same as the depth of beveled surface 736. When light travels through optical fiber 731 and out of the distal end, it will be emitted approximately perpendicular to the optical axis 732 near lateral line 733 in an angular pattern determined by the position of beveled surface 736.

Figure 7E:
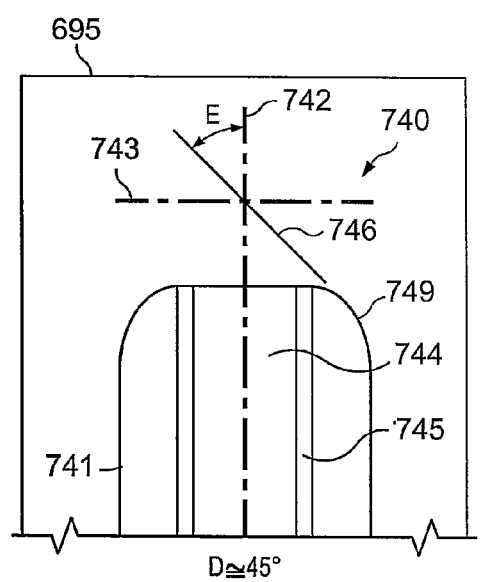

In FIG. 7e, distal optical element 740 is encased in transparent cap 695. Distal optical element 740 includes optical fiber 741 with optical axis 742 having core 744. Core 744 is surrounded by cladding 745 which is further surrounded by jacket 749. Reflecting surface 746 is positioned above the distal end of the optical fiber at an angle E where E is about 45°. When light travels through optical fiber 741 and out of the distal end, it will be emitted approximately along the optical axis 742, reflected from reflecting surface 746, and further emitted in a horizontal range of directions near lateral line 743 in an approximate angular pattern determined by the aperture of the optical fiber, the aperture of the reflecting surface and the wavelength of the emitted light. When used as an optical collector, optical fiber 741 will collect light in the approximate angular pattern from the horizontal range of direction near lateral line 743.

Figure 7F:
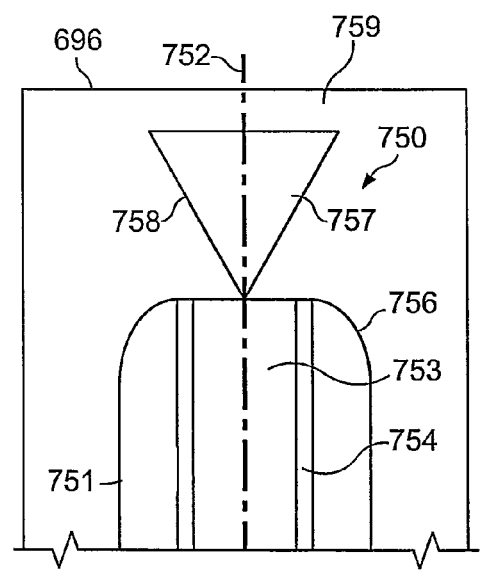

FIG. 7f, distal optical element 750 is encased by transparent cap 696. Distal optical element 750 includes optical fiber 751 with optical axis 752 and core 753. Core 753 is surrounded by cladding 754 which is further surrounded by jacket 756. Reflector 757 is positioned adjacent optical fiber 751 and coaxial with optical axis 752. In a preferred embodiment, reflector 757 is conical, that includes silvered surface 758. In use, light transmitted from the optical fiber is reflected in a 360° pattern, generally perpendicular to optical axis 752. Similarly, reflector 757 collects light from a 360° axis and transmits it through optical fiber 751, generally parallel to optical axis 752. In a preferred embodiment, transparent cap 696 is filled with an optically transparent plastic matrix which supports and positions reflector 757 above optical fiber 751. In an alternative embodiment, reflector 757 can be formed by a void in matrix 759 which is internally silvered on surface 758.

FIG. 7g, distal optical element 760 is formed as a cap 697. Distal optical element 760 includes optical fiber 761 with optical axis 762 having core 764. Core 764 is surrounded by cladding 767 which is further surrounded by jacket 769. One side of cap 697 includes a reflecting surface 768 which is positioned above the distal end of the optical fiber at an angle of about 45° from optical axis 763. When light travels through optical fiber 761 and out of the distal end, it will be emitted approximately along the optical axis 762, reflected from reflecting surface 768, and further emitted in a horizontal range of directions near lateral line 763 in an approximate angular pattern determined by the aperture of the optical fiber, the aperture of the reflecting surface and the wavelength of the emitted light. The emitted light is collimated by lens 765. When used as an optical collector, lens 765 focuses collected light as it enters cap 697. The collected light is directed by reflecting surface 768 into optical fiber 761.

Referring to FIGS. 8a-8d, a single-lead embodiment is described in situ. Spinal cord 820 is shown in various respective positions in the spinal canal in relation to a lateral (coronal) axis 824 and a postero-anterior (sagittal) axis 825 which are perpendicular to one another. Forward direction is towards 0° parallel to the postero-anterior axis, rightward direction is toward 90° parallel to the lateral axis, backward direction is toward 180°, and leftward direction is toward 270°. A stimulator lead assembly, with electrode 801 and optical element 802, is implanted outside dura 821. Optical element 802 is optically coupled to optical emitter 865 and optical detector 867. It should be understood that optical detector 867 will receive light originating from optical emitter 865 after reflection from spinal cord 820.

Electrode 801 and optical element 802 are positioned toward the dura and within an operational range of target cells 819. Target cells 819 are positioned within spinal cord 820 in an arbitrary but constant position with respect to the spinal cord.

In FIG. 8a, spinal cord 820 is in a forward position toward 0° along postero-anterior axis 825. Path $P_1$ defines a light path from optical element 802 to reflection point $R_1$ and back to optical element 802. The length of path $P_1$ is $D_1$. Optical element 802 emits light from optical emitter 865 along path $P_1$ where it is reflected at point $R_1$ by the spinal cord surface after attenuation and scattering by intermediate tissue. Optical element 802 collects light from path $P_1$ after reflection at point $R_1$ and after attenuation and scattering by intermediate tissue. Light collected by optical element 802, is detected by photodetector 867 and converted to photocurrent $I_1$.

In FIG. 8b, spinal cord 820 is in a rightward position with respect to optical element 802, rotated by angle 828 from postero-anterior axis 825 where target cells 819 are shifted rightward toward 90° and parallel to lateral axis 824 by distance 827. Path $P_2$ defines a light path from optical element 802 to reflection point $R_2$ and back to optical element 802. The length of path $P_2$ is $D_2$ which is less than $D_1$. Optical element 802 emits light from optical emitter 865 along path $P_2$ where it is reflected at point $R_2$ by the spinal cord surface after attenuation and scattering by intermediate tissue. Optical element 802 collects light from path $P_2$ after reflection at point $R_2$ and after attenuation and scattering by intermediate tissue. Light collected by optical element 802, is detected by photodetector 867 and converted to photocurrent $I_2$.

In FIG. 8c, spinal cord 820 is in a posterior position shifted by a distance 826 towards optical element 802 along postero-anterior axis 825. Path $P_3$ defines a light path from optical element 802 to reflection point $R_3$ and back to optical element 802. The length of path $P_3$ is $D_3$ which is less than $D_1$ or $D_2$. Optical element 802 emits light from optical emitter 865 along path $P_3$ where it is reflected at point $R_3$ by the spinal cord surface after attenuation and scattering by intermediate tissue. Optical element 802 collects light from path $P_3$ after reflection at point $R_3$ and after attenuation and scattering by intermediate tissue. Light collected by optical element 802, is detected by photodetector 867 and converted to photocurrent $I_3$.

In FIG. 8d, spinal cord 820 is in a left position with respect to optical element 802, rotated by angle 830 from postero-anterior axis 825 where target cells 819 are shifted leftward along lateral axis 824 by distance 829. Path $P_4$ defines a light path from optical element 802 to reflection point $R_4$ and back to optical element 802. The length of path $P_4$ is $D_4$ which is less than $D_1$, but about the same as $D_2$. Optical element 802 emits light from optical emitter 865 along path $P_4$ where it is reflected at point $R_4$ by the spinal cord surface after attenuation and scattering by intermediate tissue. Optical element 802 collects light from path $P_4$ after reflection at point $R_4$ and after attenuation and scattering by intermediate tissue. Light collected by optical element 802, is detected by photodetector 867 and converted to photocurrent $I_4$.

Since $D_2$ and $D_4$ are less than $D_1$, the photocurrents $I_2$ and $I_4$ are observed to be greater than $I_1$. Since $D_3$ is less than $D_1$, $D_2$ or $D_4$ the light is attenuated less, and the photocurrent $I_3$ is observed to be greater than $I_1$, $I_2$ or $I_4$.

An electric field produced by the electrode 801 stimulates target cells 819 in the spinal cord 820. Current amplitude is the average current supplied the set of electrodes, each having pulse width PW and pulse frequency PF. For the position of the spinal cord in FIG. 8a, the current amplitude has a value of about $A_1$. For the rightward shifted position of the spinal cord in FIG. 8b, the current amplitude has a value of about $A_2$ which is about the same as $A_1$. For the back shifted position of the spinal cord in FIG. 8c, the current amplitude has a value of about $A_3$ which is less than $A_1$. For the leftward shifted position of the spinal cord in FIG. 8d, the current amplitude has a value of $A_4$ which is about the same as $A_1$. Comparing the electrode currents for the positions of FIGS. 8a-d, $A_3 < (A_2 \approx A_4) < A_1$ which is correspondingly displayed on the plot of FIG. 5 and where electrode current is proportional to electric field strength. The foregoing results are tabulated in Table 1.

TABLE 1

| Position | Photodetector Signal, I | Current Amplitude, A |
|---|---|---|
| 1. Front 0° | L | H |
| 2. Right 90° | M | M |
| 3. Back 180° | H | L |
| 4. Left 270° | M | M |

Figures 9A, 9B:
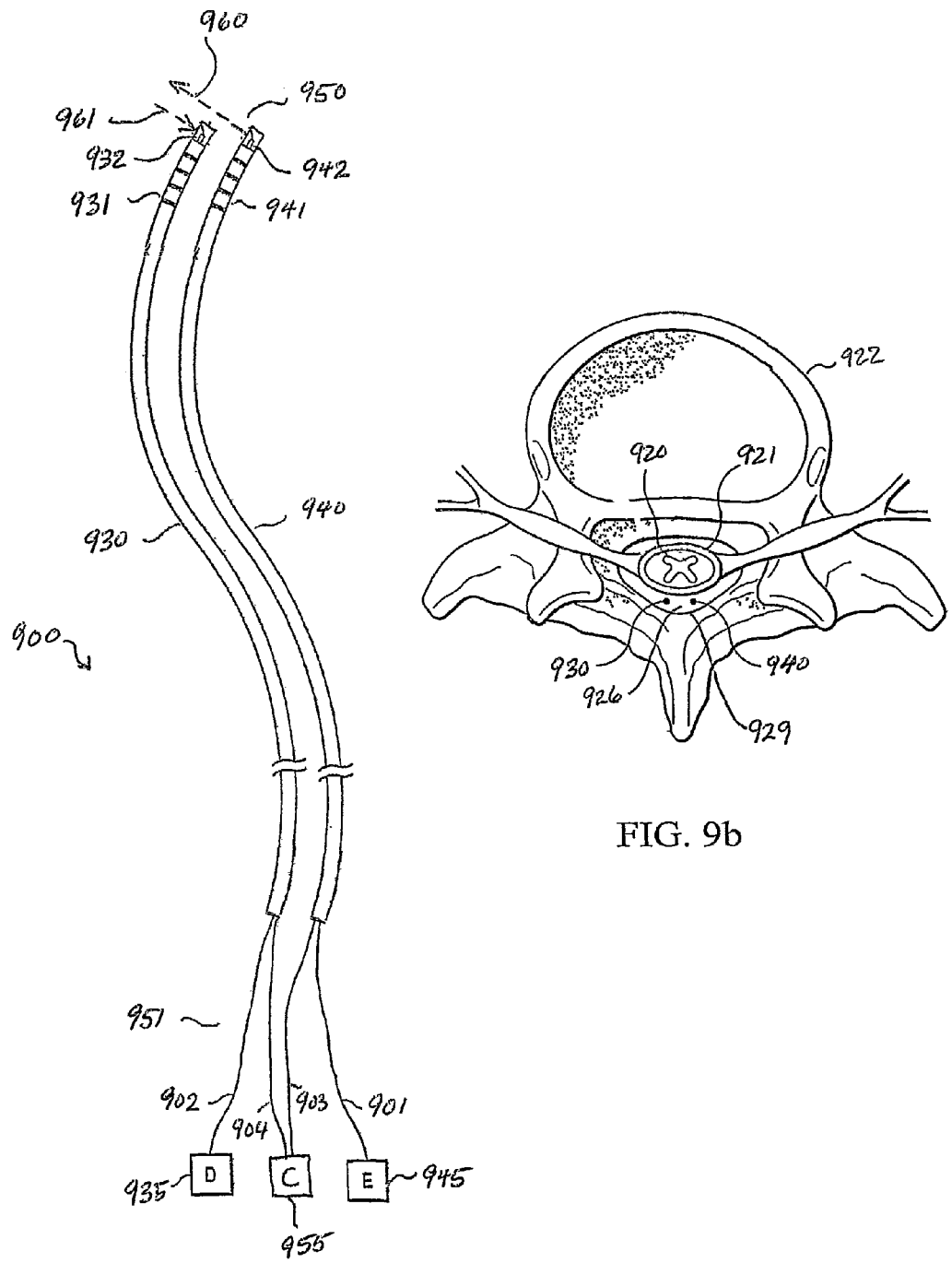
FIG. 9a shows a dual stimulator lead embodiment having one optical fiber operating as an optical emitter and another optical fiber operating as an optical collector.
FIG. 9b shows placement of two stimulator leads in a dual stimulator lead embodiment.

Referring to FIG. 9a, a preferred embodiment of a dual-lead configuration suitable for a stimulator lead system 900 is shown. Stimulator lead 930 includes optical fiber 902 coupled to optical element 932 at distal end 950 and coupled to optical detector 935 at the proximal end 951. Optical element 932 is configured as an optical collector. A set of electrodes 931, near the distal end, is coupled to a current source 955 through a set of leads 904 also included in stimulator lead 930.

Stimulator lead 940 includes optical fiber 901 coupled to optical element 942 at the distal end and coupled to optical emitter 945 at the proximal end. Optical element 942 is configured as an optical emitter. A set of electrodes 941, near the distal end, is coupled to a current source 955 through a set of leads 903 also included in the stimulator lead 940.

Probe light beam 960 emitted from optical emitter 945 propagates through optical fiber 901 and exits from optical element 942. A responsive light beam 961 collected by optical element 932, propagates through optical fiber 902, is detected by optical detector 935 and converted to a photocurrent signal. The photocurrent signal is processed to determine an amount of current to supply to electrodes 931 and 941.

Referring to FIG. 9b, where vertebra 922 houses spinal cord 920, stimulator leads 930 and 940 are placed side by side in the epidural space 926 between the dura 921 and the walls of the spinal canal 929.

To operatively place the two stimulator leads, a first stimulator lead is positioned into the epidural space near the spinal cord using a wire stylus inserted in a lumen of the first stimulator lead. The wire stylus is withdrawn and an optical fiber assembly is inserted in the lumen. Then, a second stimulator lead is positioned in the epidural space near the spinal cord and to the side of the first stimulator lead using the wire stylus inserted in a lumen of the second stimulator lead. The wire stylus is withdrawn and an optical fiber assembly is inserted in the lumen.

Referring to FIGS. 10a-10d, a dual-lead embodiment, utilizing the stimulator leads of FIG. 9, is described as in situ. Spinal cord 1020 is shown in various respective positions in the spinal canal in relation to a coronal axis 1024 which is centered through optical emitter 1041 and optical collector 1031. A sagittal axis 1025 is perpendicular to the coronal axis and generally in the postero-anterior direction of the body encapsulating spinal cord 1020. Forward direction is towards 0° parallel to the sagittal axis, rightward direction is toward 90° parallel to the coronal axis, backward direction is toward 180°, and leftward direction is toward 270°.

Stimulator lead assembly 1010 is implanted outside dura 1021 having a left stimulator lead with electrode 1041 and optical element 1042 and having a right stimulator lead with electrode 1031 and optical element 1032. Optical element 1042 is optically coupled to optical emitter 1045. Optical element 1032 is optically coupled to optical detector 1035. It should be understood that optical detector 1035 will receive light originating from optical emitter 1045. In situ, the stimulator lead positions may be reversed where the stimulator lead with optical element 1032 and electrode 1031 is on the left and the stimulator lead with optical element 1042 and electrode 1041 is on the right.

Electrodes 1031 and 1041 are positioned toward the dura and within an operational range of target cells 1019. Target cells 1019 are positioned within spinal cord 1020 in an arbitrary but constant position with respect to the spinal cord.

Referring to FIG. 10a, the spinal cord is positioned forward, path $P_5$ defines a light path from optical element 1042 to reflection point $R_5$ and then to optical element 1032. The length of path $P_5$ is $D_5$. Optical element 1042 emits light along path $P_5$ from optical emitter 1045 and optical element 1032 collects light from path $P_5$ after reflection at point $R_5$ from spinal cord 1020 and after attenuation and scattering by intermediate tissue. Light collected by optical element 1032 is detected by photodetector 1035 which produces a photocurrent of $I_1$ in response.

An electric field produced by electrodes 1031 and 1041 stimulates target cells 1019. Current amplitudes $A_{R1}$ and $A_{L1}$ are for the average currents supplied by electrode 1031 and electrode 1041, respectively having pulse widths $PW_1$ and pulse frequencies $PF_1$. For the position of the spinal cord in FIG. 10a, given a fixed pulse width $PW_1$ and a fixed pulse frequency $PF_1$, the current amplitudes $A_{R1}$ and $A_{L1}$ are approximately the same. These foregoing results are tabulated in Table 2, row 1.

Referring to FIG. 10b, the spinal cord is rotated through angle 1028 and positioned rightward by a distance 1027 towards 90°, path $P_6$ defines a light path from optical element 1042 to reflection point $R_6$ and then to optical element 1032. The length of path $P_6$ is $D_6$ which is less than the length $D_5$. Optical element 1042 emits light along path $P_6$ from optical emitter 1045 and optical element 1032 collects light from path $P_6$ after reflection at point $R_6$ from spinal cord 1020 and after attenuation and scattering by intermediate tissue. Light collected by optical element 1032 is detected by photodetector 1035 which produces a photocurrent of $I_2$ in response where $I_2$ is greater than $I_1$.

An electric field produced by electrodes 1031 and 1041 stimulates target cells 1019. Current amplitude $A_{R2}$ is for the average current supplied by electrode 1031 and current amplitude $A_{L2}$ is for the average current supplied by electrode 1041, each having pulse widths $PW_2$ and pulse frequencies $PF_2$. The current amplitudes $A_{R2}$ and $A_{L2}$ are greater than current amplitudes $A_{RI}$ and A. These foregoing results are tabulated in Table 2, row 2.

Referring to FIG. 10c, the spinal cord is positioned towards the back and displaced by a distance 1026 towards 180°, path $P_7$ defines a light path from optical element 1042 to reflection point $R_7$ and then to optical element 1032. The length of path $P_7$ is $D_7$ which is shorter than length $D_5$ or $D_6$. Optical element 1042 emits light along path $P_7$ from optical emitter 1045 and optical element 1032 collects light from path $P_7$ after reflection at point $R_7$ from spinal cord 1020 and after attenuation and scattering by intermediate tissue. Light collected by optical element 1032 is detected by photodetector 1035 which produces a photocurrent of $I_3$ in response, where $I_3$ is greater than $I_1$ and $I_2$.

An electric field produced by electrodes 1031 and 1041 stimulates target cells 1019. Current amplitude $A_{R3}$ is for the average current supplied by electrode 1031 and current amplitude $A_{L3}$ is for the average current supplied by electrode 1041, each having pulse widths $PW_3$ and pulse frequencies $PF_3$. The current amplitudes $A_{R3}$ and $A_{L3}$ are less than the current amplitudes $A_{R1}$, $A_{R2}$, $A_{L1}$ and $A_{L2}$. These foregoing results are tabulated in Table 2, row 3.

Referring to FIG. 10d, the spinal cord is rotated through angle 1030 and positioned rightward by a distance 1029 towards 270°, path $P_8$ defines a light path from optical element 1042 to reflection point $R_8$ and then to optical element 1032. The length of path $P_8$ is $D_8$ which is less than length $D_5$ but about the same as $D_6$. Optical element 1042 emits light along path $P_8$ from optical emitter 1045 and optical element 1032 collects light from path $P_8$ after reflection at point $R_8$ from spinal cord 1020 and after attenuation and scattering by intermediate tissue. Light collected by optical element 1032 is detected by photodetector 1035 which produces a photocurrent of $I_4$ in response where $I_4$ is about the same as $I_2$.

An electric field produced by electrodes 1031 and 1041 stimulates target cells 1019. Current amplitude $A_{R4}$ is for the average current supplied by electrode 1031 and current amplitude $A_{L4}$ is for the average current supplied by electrode 1041, each having pulse widths $PW_2$ and pulse frequencies $PF_2$. The current amplitudes $A_{R4}$ and $A_{L4}$ are about the same as the current amplitudes $A_{R1}$ and $A_{L1}$. These foregoing results are tabulated in Table 2, row 4.

The distances $D_6$ and $D_8$, defining optical paths for the light emitted by the optical emitter and collected by the optical collector, are less than the distance $D_5$. The distance $D_7$ is smaller than the distances $D_5$, $D_6$ and $D_8$. Comparing photocurrents of positions of FIGS. 10a through 10d, $I_3 > (I_2 \approx I_4) > I_1$.

The relative relationship between received photodetector currents and required current amplitudes of the current signals to the electrodes, $A_L$ and $A_R$, can be summarized in the following table for the four example positions of the spinal cord in the spinal canal.

TABLE 2

| Position | Photodetector Signal, I | Current Amplitude, $A_R$ | Current Amplitude, $A_L$ |
| --- | --- | --- | --- |
| 1. Front 0° | L | H | H |
| 2. Right 90° | M | M | M |
| 3. Back 180° | H | L | L |
| 4. Left 270° | M | M | M |

Figure 11:
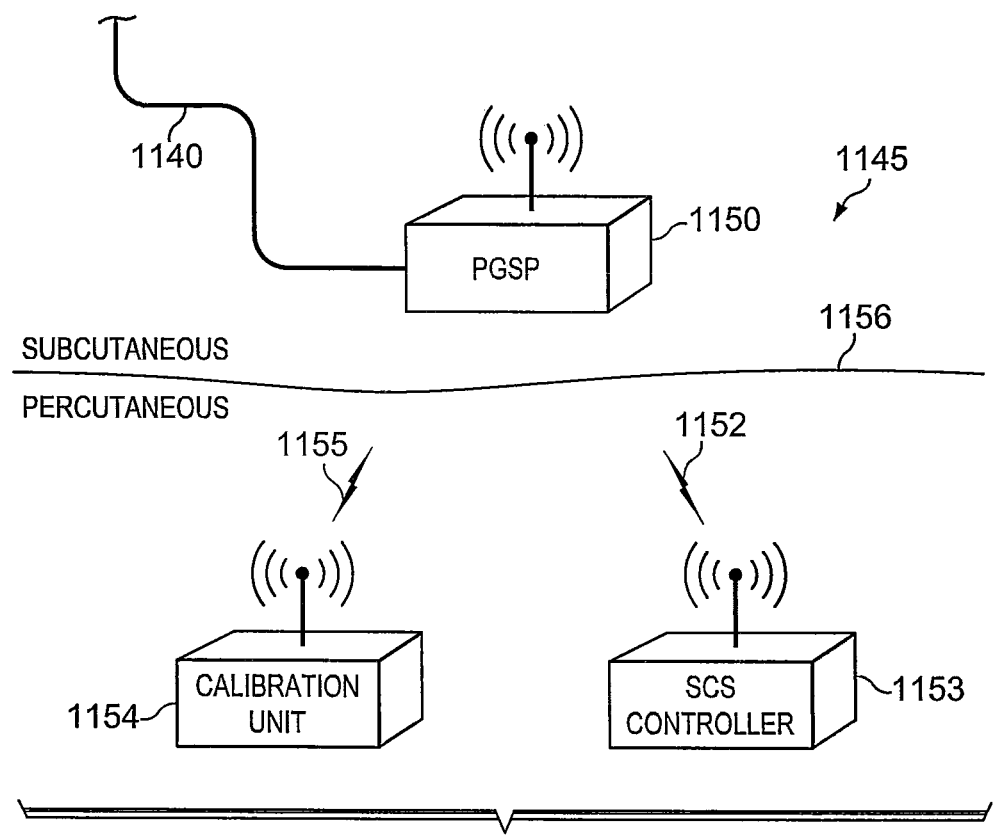
FIG. 11 shows a schematic representation of a preferred embodiment of the positionally sensitive spinal cord stimulation system.

Referring to FIG. 11, a preferred embodiment of the components of the system is shown. Stimulator lead assembly 1140 includes at least one stimulator lead with a set of electrodes. Positionally-sensitive spinal cord stimulator 1145 includes pulse generator and signal processor (PGSP unit) 1150 and is connected to stimulator lead assembly 1140. PGSP unit 1150 provides power to the set of electrodes in stimulator lead assembly 1140 and houses electronic and opto-electronic components of the system. Stimulator lead assembly 1140 connects to PGSP unit 1150 further connecting the stimulator electrodes of each stimulator lead to a controllable current source. Stimulator lead assembly 1140 connects at least one IR emitter to at least one optical fiber through a first fiber optical connector and at least one photodetector to at least one optical fiber through additional fiber optic connectors.

PGSP unit 1150 gathers and processes photodetector signals and makes adjustments to the stimulator electrode current (or voltage) based on the photodetector signals. PGSP unit 1150 is connected by wireless communication link 1152 across skin boundary 1156 to SCS controller 1153. The SCS controller is configured to allow percutaneous activation of and adjustments to positionally-sensitive spinal cord stimulator 1145. PGSP unit 1150 is also connected by wireless communication link 1155 to calibration and programming unit 1154. Calibration and programming unit 1154 is programmed to accept patient input and transmit the patient input to PGSP 1150 during calibration. In an alternate embodiment, calibration and programming unit 1154 is incorporated into SCS controller 1153.

PGSP unit 1150 is preferably powered by batteries. In an alternate embodiment, PGSP unit 1150 derives power from capacitive or inductive coupling devices. Calibration may further calibrate the batteries, the capacitive devices, or inductive coupling in PGSP unit 1150. Communication links 1152 or 1155 may further serve as a means of providing electrical charge for the batteries or capacitive devices of PGSP unit 1150.

Figure 12:
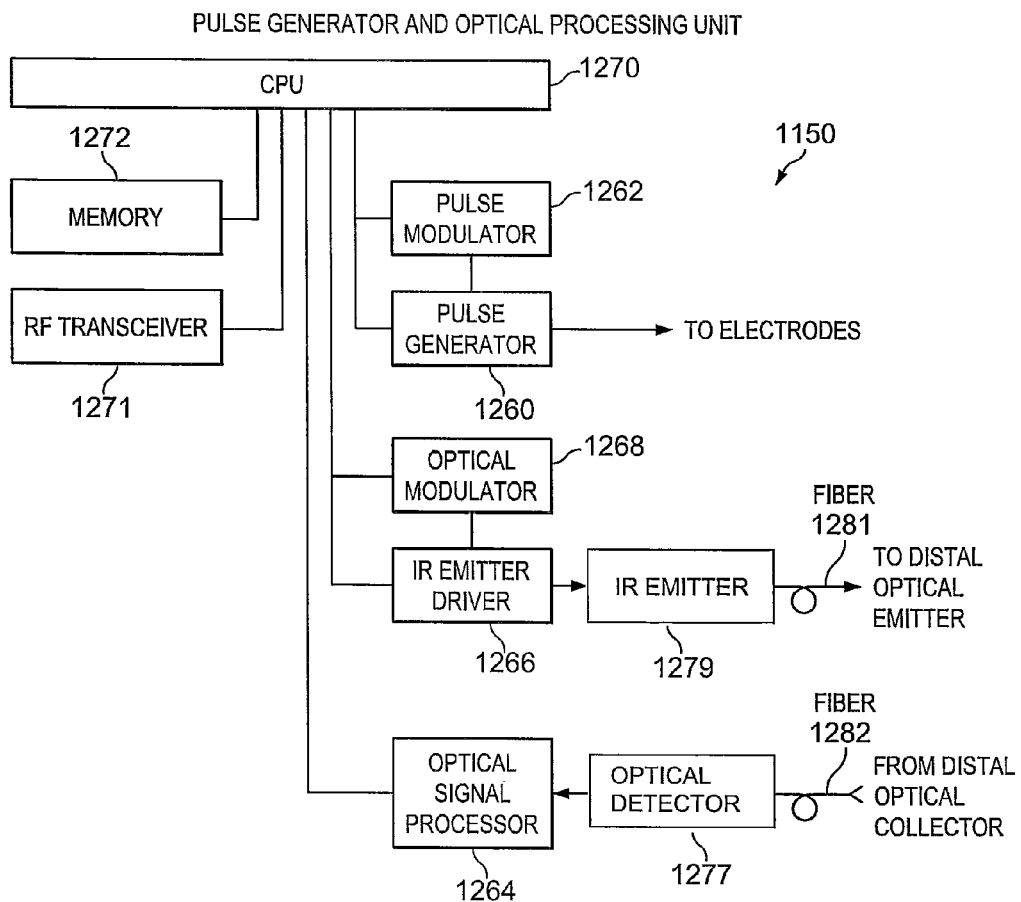
FIG. 12 is a block diagram of the components of a preferred embodiment of a pulse generation and optical signal processing unit.

Referring to FIG. 12, block diagram of PGSP unit 1150 is shown. PGSP unit 1150 includes CPU 1270 having onboard memory 1272. CPU 1270 is connected to pulse modulator 1262 and pulse generator 1260. Pulse modulator 1262 is connected to pulse generator 1260. CPU 1270 is also operatively connected to optical modulator 1268 and optical signal processor 1264. Optical modulator 1268 is connected to infrared emitter driver 1266. Infrared emitter driver 1266 is connected to IR emitter 1279 and drives IR emitter 1279. IR emitter 1279, includes a fiber optic connector to effectively couple IR emitter 1279 to optical fiber 1281. Optical fiber 1281 is connected to a distal optical emitter in a stimulator lead of the stimulator lead assembly.

CPU 1270 is also connected to optical signal processor 1264. Optical signal processor 1264 is connected to photodetector 1277 and receives an optical signal from the photodetector, filters the optical signal, and correlates the optical signal to electrode current amplitude, pulse width and frequency. Optical signal processor 1264 may include a synchronized gated detection (e.g., lock-in amplifier type) function or other demodulation function to improve the signal to noise ratio of the detected light.

IR detector 1277 is connected to optical signal processor 1264 and optical fiber 1282. IR detector 1277 translates incoming light pulses from optical fiber 1282 into electrical signals which are processed by optical signal processor 1264. Optical fiber 1282 is coupled to a distal optical collector in a stimulator lead of the stimulator lead assembly.

In a preferred embodiment, the photodetector is similar to that of Part No. OP501 from Optek Technology.

CPU 1270 is connected to optical modulator 1268. IR emitter driver 1266 is connected to both optical modulator 1268 and CPU 1270. In operation, CPU 1270 activates optical modulator 1268 which generates a waveform and transmits the waveform to the IR emitter driver 1266. The IR emitter driver then causes IR emitter 1279 to launch a pulse with the waveform into optical fiber 1281.

The optical waveform may take several forms. For example, the pulse width of the optical waveform may have a low duty cycle to minimize power consumption. A single optical pulse may occur for a set of electrode stimulation pulses. The optical waveform may include frequency, phase or amplitude modulation. Typical wavelength of the IR light from the IR emitter is in a range from 800 nm to 870 nm. Typical output intensity of the IR emitter is 1 to 2 mW and a suitable part is Part No. VSMY1859 from Vishay Intertechnology, Inc.

Pulse generator 1260 is connected to the set of electrodes in stimulator lead assembly 1140. In order to generate a pulse to the electrodes, CPU 1270 consults a calibration table stored in onboard memory 1272 to determine pulse width PW, pulse frequency Pf and pulse amplitudes for the set of electrodes, respectively. The pulse width and frequency are transmitted to pulse modulator 1262 which creates a modified square wave signal. The modified square wave signal is passed to pulse generator 1260. CPU 1270 passes the amplitudes for the set of electrodes to pulse generator 1260 in digital form. Pulse generator 1260 then amplifies the modified square waves according to the pulse amplitudes and transmits them to the set of electrodes. CPU 1270 is in transcutaneous communications, via RF transceiver 1271, with calibration and programming unit 1154 and SCS controller 1153.

The modified square wave has an amplitude and duration (or width). Pulse widths varying from 20 to 1000 microseconds have been shown to be effective. The frequency of the pulse waveforms between 20 and 10,000 hertz have been shown to be effective. The output amplitude is preferably from 0 (zero) to +/−20 mA or 0 (zero) to +/−10 V but may vary beyond those ranges according to patient sensitivity.

Figure 13:
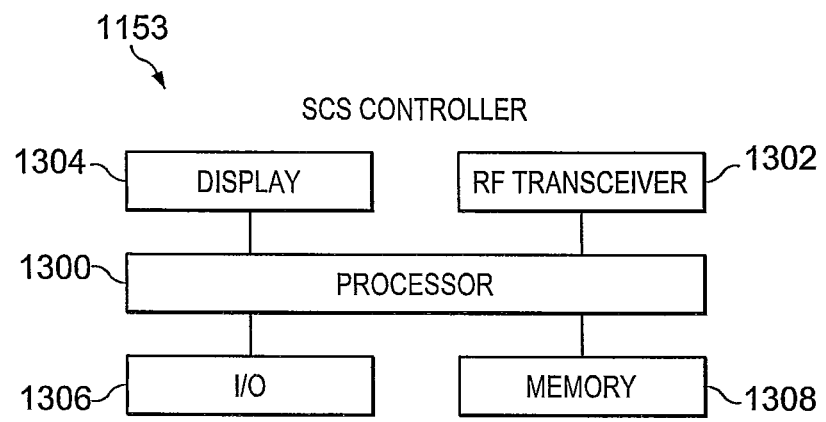
FIG. 13 is a block diagram of the components of a preferred embodiment of an SCS controller.

Referring to FIG. 13, SCS controller 1153 is shown. SCS controller 1153 includes processor 1300 connected to RF transceiver 1302, to display 1304, to input/output device 1306 and to memory 1308. In the preferred embodiment, display 1304 is a low power liquid crystal display adapted to show the current operational state of the system. I/O device 1306 is a simple push button contact array which is constantly monitored by processor 1300. In the preferred embodiment, RF transceiver 1302 is a low power transmitter/receiver combination.

Figure 14:
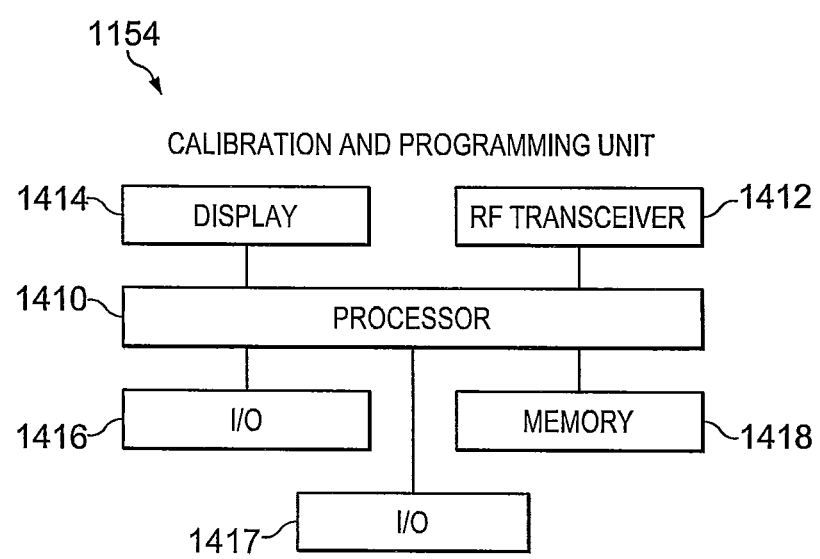
FIG. 14 is a block diagram of the components of a preferred embodiment of a calibration and programming unit.

Referring to FIG. 14, calibration and programming unit 1154 will be described. Calibration and programming unit 1154 includes processor 1410 connected to onboard memory 1418, to input/output devices 1416 and 1417, to RF transceiver 1412 and to display 1414. Display 1414, in the preferred embodiment, is a low power liquid crystal display. Input/output device 1416 and input/output device 1417 are simple push button switches monitored continuously by the processor. RF transceiver 1412 is a low power transmitter/receiver combination.

Figure 15A:
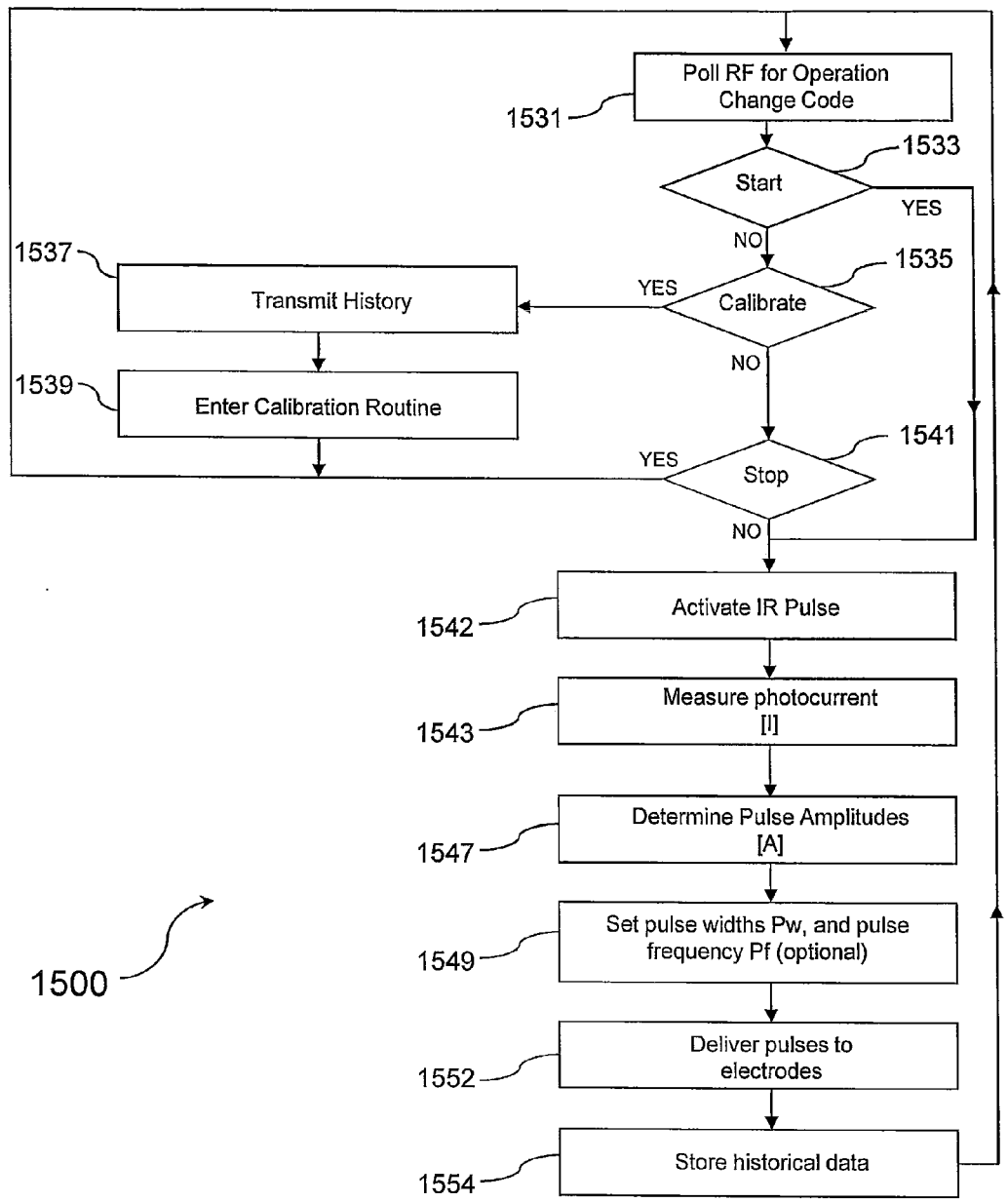
FIGS. 15a and 15b are flow diagrams of a method of operation of a preferred embodiment.
Figure 15B:
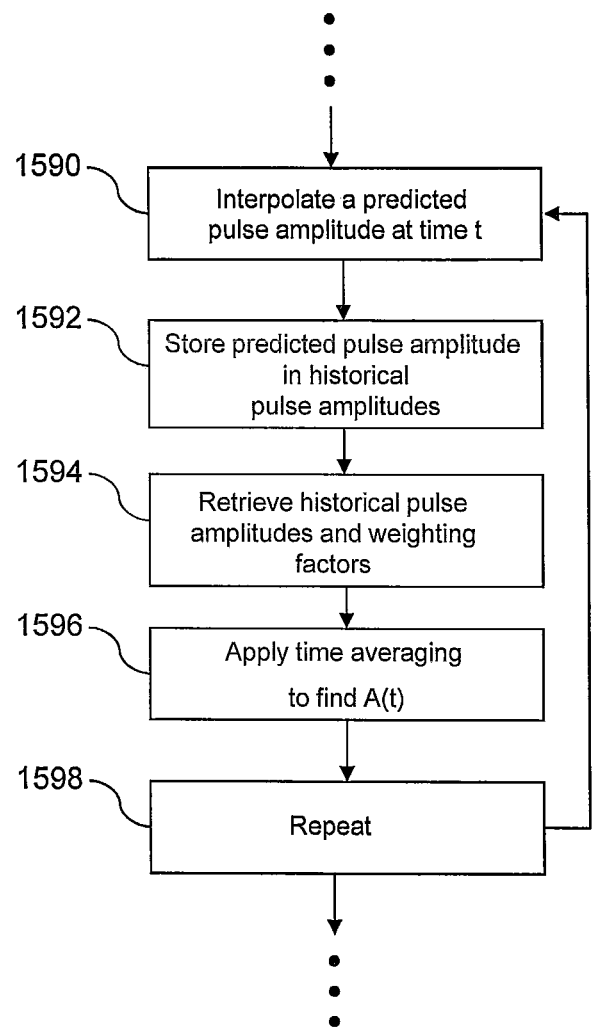

Referring to FIGS. 15a-15b, method 1500 of operation of the positionally-sensitive spinal cord stimulator of FIG. 12 is shown. In the preferred embodiment, method 1500 takes the form of a computer program which is resident in memory 1272 of CPU 1270 of PGSP 1150. When activated, the program forms a continuous cycle.

Referring to FIG. 15a, at step 1531, RF transceiver 1271 is continually polled for a change of operation code signal to be received from SCS controller 1153. One of three options is always present, "start?", "calibrate?" and "stop?"

At step 1533, if operation change code "start?" is received, the method moves to step 1542. At step 1542, CPU 1270 activates optical modulator 1268, which in turn activates IR emitter driver 1266 to generate an optical pulse from the IR emitter. At step 1543, a set of photocurrent levels for a photodetector [I] is measured by optical signal processor 1264 and passed to CPU 1270 for storage in memory.

At step 1547, the CPU determines a set of amplitudes [A] of a train of pulses to be sent to the set of electrodes, based on the photocurrent level and a calibration table. In step 1547, the set of amplitudes are interpolated from the calibration table using the photocurrent level. At step 1549, optionally, the CPU sets the values of the pulse width $P_W$ and frequency $P_f$ of the pulse train to be sent to the set of electrodes.

At step 1552, the CPU activates the pulse modulator to create the waveforms of the pulse trains to be sent to the set of electrodes and then activates pulse generator 1260 to generate the pulse trains. At step 1554, the CPU stores the values of [I], [A], $P_W$ and $P_f$ in a time series of data in memory for future retrieval. The method then returns to step 1531.

If at step 1533, the operation change code is not "start?", the method proceeds to step 1535. At step 1535, the CPU determines if the operation change code is "calibrate?" If so, the method moves to step 1537. At step 1537, the CPU transmits the time series of data to calibration and programming unit 1154. At step 1539, the CPU enters the calibration routine as will be described more fully below. The method then returns to step 1531.

If at step 1535, the operation change code is not "calibrate?", the method moves to step 1541. At step 1541, the CPU determines if the operation change code is "stop?". If so, the method returns to step 1531. If not, the method proceeds to step 1542 and continues as previously described.

In the preferred embodiment, the pulse width and frequency is kept constant for a given patient and only the set of electrode amplitudes are varied. In another embodiment, step 1549 is performed whereby pulse width and pulse frequency are dynamically varied according to the calibration values stored in the calibration table for each electrode.

Referring to FIG. 15b, an alternate embodiment of determining amplitude values, at step 1547 is shown. At step 1590, the CPU performs interpolation to determine a predicted amplitude at time t from the photocurrent level. At step 1592, the predicted amplitude is stored into a set of historical amplitudes which are predicted amplitudes for times $t_i$<t. At step 1594, the CPU time averages historical amplitudes from the time series of data to determine a new set of electrode amplitudes. At step 1594, the CPU also obtains a set of predetermined weighting factors w from memory.

At step 1596, the following equation is applied:

$$A_j(\text{delivered}) = \frac{w_k \cdot A_j(k) + w_{k-1} \cdot A_j(k-1) + w_{k-2} \cdot A_j(k-2) + \ldots}{w_k + w_{k-1} + w_{k-2} + \ldots} \quad \text{(Eq. 3)}$$

where $w_k$=predetermined weight for the values of $A_j$ at the current time k and earlier times k−1, k−2, . . . , etc., and where $A_j$=jth electrode amplitude. At step 1598, if there are separate left and right electrode amplitudes, steps 1590, 1592, 1594 and 1596 are repeated for each electrode.

Figure 16:
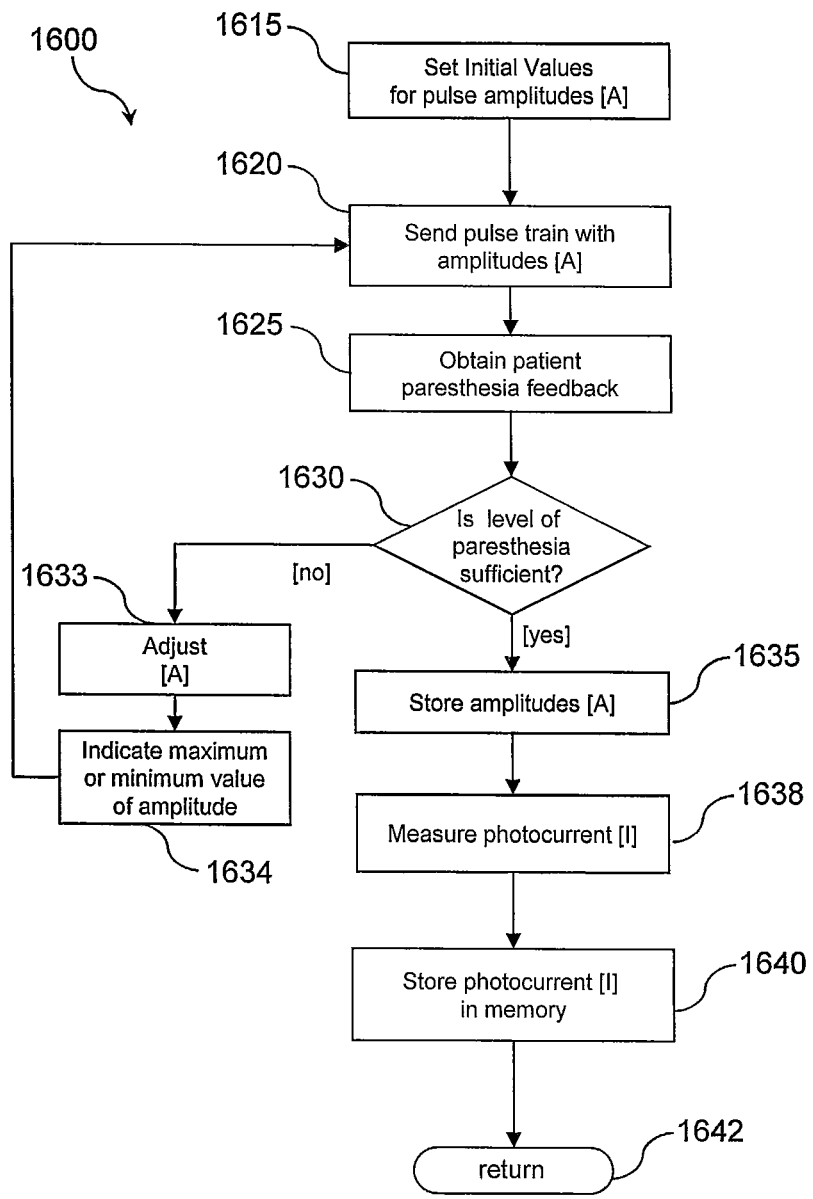
FIG. 16 is a flow diagram of a preferred method of calibration.

Referring to FIG. 16, the processor is programmed to carry out steps of calibration method 1600 upon request by a calibration control program. At step 1615, each current amplitude in a set of current amplitudes [A] are adjusted to an initial value, preferably the minimum value of a predetermined range. At step 1620, the pulse generator is directed by the CPU to send a train of pulses to each electrode at the minimum values. At step 1625, paresthesia feedback is solicited from the patient to determine a level of paresthesia. At step 1630, it is determined if the level of paresthesia is sufficient and optimal for patient.

If the level of paresthesia is not optimal according to the patient feedback, then the method moves to step 1633. At step 1633, the processor monitors the input/output device to determine if amplitude values need to be increased or decreased, or if the level of paresthesia is sufficient. If an amplitude value needs to be adjusted, then the amplitude value is correspondingly increased or decreased by a discrete amount. If the amplitude value reaches a maximum level or a minimum level and cannot be adjusted further, step 1634 is performed where an alert is indicated by the calibration and programming unit. The alert in step 1634 may be a visual indication, audio indication or both visual and audio indication.

After adjustment of the amplitude values, step 1620 is repeated, and a train of pulses is delivered to each electrode at the new amplitude levels. At step 1625, patient paresthesia feedback is again solicited. If, at step 1630, the level of paresthesia is still not optimal according to the patient feedback, the method repeats steps 1633 and 1634 as required. If, at step 1630, the level of paresthesia is sufficient according to patient feedback, the method moves to step 1635.

At step 1635, the CPU stores the new amplitude levels for the electrodes. At step 1638, the optical signal processor measures the photocurrent [I] for the photodetector and transfers the corresponding photocurrent value to the CPU. At step 1640, the photocurrent [I] and amplitude levels [A] are recorded in a calibration table. At step 1642, the calibration method steps complete by returning control to the calibration control program.

Figure 17:
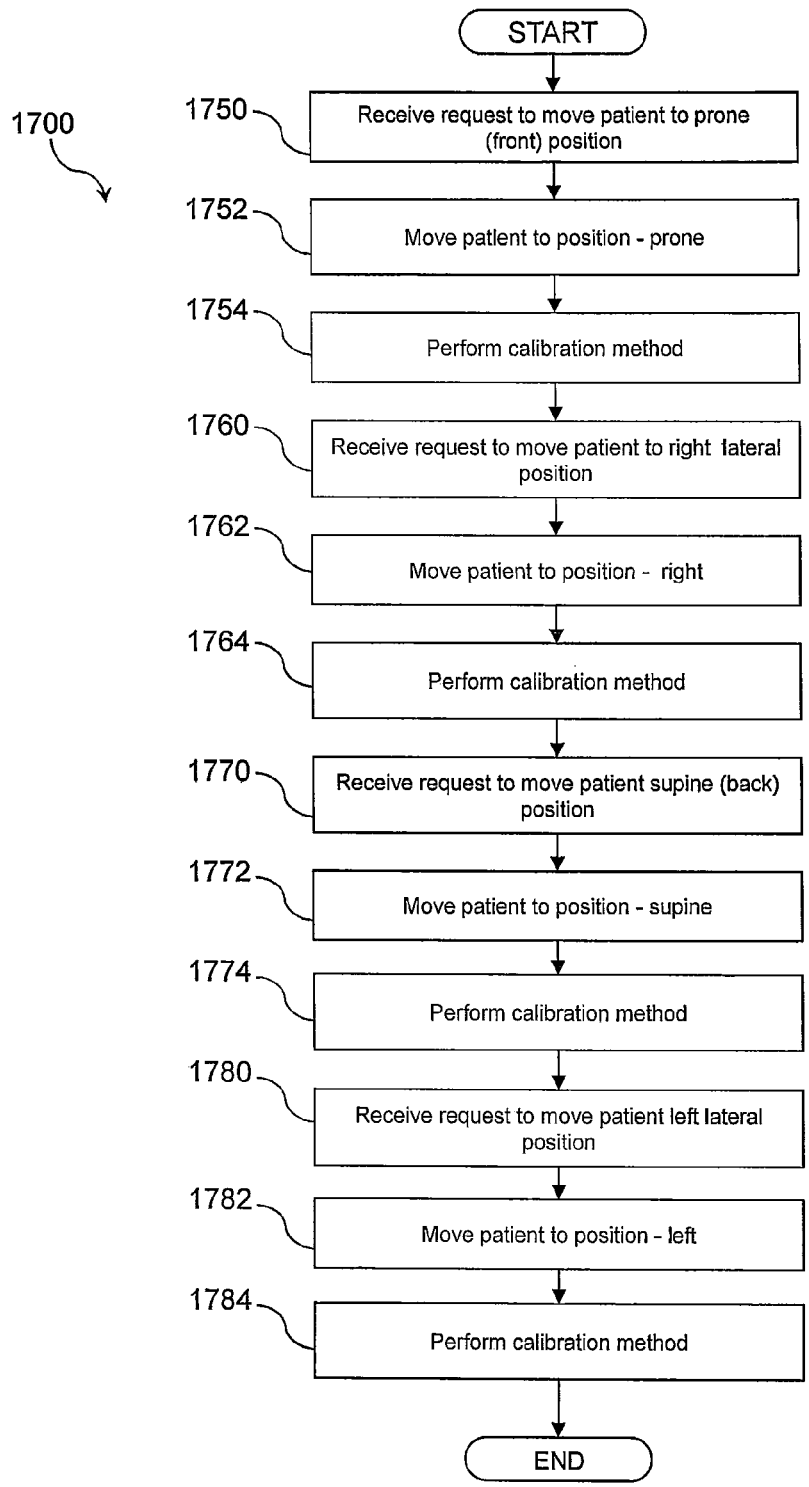
FIG. 17 is a flow diagram of a preferred method of calibration for a particular patient.

Referring to FIG. 17, the processor of the calibration and programming unit is programmed to further carry out the following method steps for a calibration control program 1700 in cooperation with physical motion of the patient.

At step 1750, RF transceiver 1412 receives a signal indicative of a request to move the patient to a prone position and passes it to the calibration processor 1410. At step 1752, the patient is positioned in a prone position. At step 1754, calibration method 1600, is carried out to optimize the level of paresthesia experienced by the patient.

At step 1760, RF transceiver 1412 receives a signal indicative of a request to move the patient to a right lateral position and passes it to processor 1410. At step 1762, the patient is positioned in a right lateral position. At step 1764, calibration method 1600 is then carried out to optimize the level of paresthesia experienced by the patient.

At step 1770, RF transceiver 1412 receives a signal indicative of a request to move the patient to a supine position and passes it to processor 1410. At step 1772, the patient is positioned in a supine position. At step 1774, calibration method 1600 is then carried out to optimize the level of paresthesia experienced by the patient.

At step 1780, RF transceiver 1412 receives a signal indicative of a request to move the patient to a left lateral position and passes it to processor 1410. At step 1782, the patient is positioned in a left lateral position. At step 1784, calibration method 1600 is then carried out to optimize the level of paresthesia experienced by the patient.

After steps 1780, 1782 and 1784 are performed, the calibration program is complete.

The order of patient positions in calibration program 1700 may be changed in alternative embodiments. Additional patient positions may be added to calibration program 1700 in alternative embodiments, for example, the patient may be rotated clockwise to calibrate a level of paresthesia required for a clockwise position. The result of carrying out a calibration using methods 1600 and 1700 is a calibration table with each record having a stored patient position, at least one photocurrent level and at least one corresponding electrode amplitude.

Figure 18:
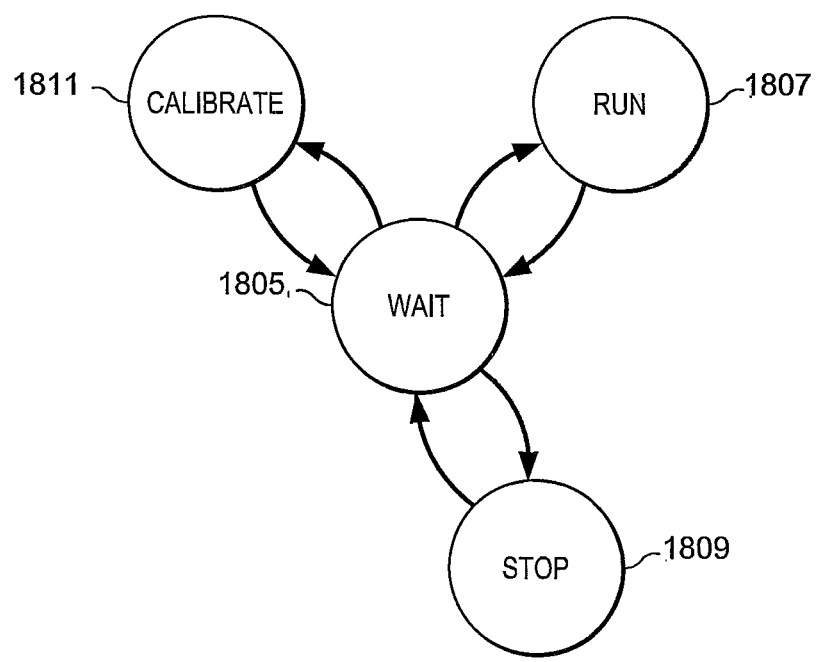
FIG. 18 is a state diagram of a preferred embodiment of stimulator control system.

Referring to FIG. 18, the various states of the SCS controller in operation will be described with the SCS controller apparatus. At wait state 1805, SCS controller 1153 enters a waiting posture and continually polls I/O device 1306. Upon receipt of a "run" signal from I/O device 1306, processor 1300 enters "run" state 1807 and transmits a "run" signal to RF transceiver 1302. RF transceiver 1302 then transmits the "run" signal to PGSP 1150 for further action. After transmission, the processor returns to wait state 1805.

If a "stop" signal is received from I/O device 1306, at step 1809, processor 1300 passes a "stop" signal to RF transceiver 1302, which in turn sends the "stop" signal to PGSP 1150. The processor then returns to wait state 1305.

If a "calibrate" signal is received from I/O device 1306, at step 1811, processor 1300 transmits a "calibrate" signal to RF transceiver 1302, which in turn sends the "calibrate" signal to PGSP 1150. Processor 1300 then returns to wait state 1805.

FIG. 19 shows a calibration table 1940 suitable for a single stimulator lead system, as shown in FIGS. 6*a-d*, with a single optical collector, a single optical emitter and a set of electrodes. Each row is a record for the optimal electrode settings for a patient position. Calibration table 1940 includes five columns for patient position identifier 1942, photodetector value 1944 for photocurrent from light detected by the optical collector, electrode stimulation pulse amplitude 1946, electrode stimulation pulse width 1948, and electrode stimulation pulse frequency 1950.

Patient position identifier 1942 in a preferred embodiment includes four positions, forward (prone)—0°, right—90°, left—270°, back (supine—180°). Each row in calibration table 1940 is associated with one of the four patient positions. Electrode stimulation pulse amplitude 1946 includes values which are derived during calibration and recorded for different spinal cord positions, corresponding to the patient position. In the preferred embodiment, the electrode stimulation pulse amplitude 1946 prescribes a stimulation energy to neurons in the vicinity of spinal cord.

To construct table 1940, calibration methods 1600 and 1700 are performed to identify a set of stimulator lead values for the pulse amplitude, width and frequency with a set of photocurrent levels.

FIG. 20 shows a calibration table 2040 suitable for a dual stimulator lead system, having one lead with a single optical emitter, having another lead with a single optical detector. Both leads have electrodes sharing the same current pulse width and frequency, but have different pulse amplitudes for each lead. Each row is a record for the optimal electrode settings for a patient position. Calibration table 2040 includes six columns for patient position identifier 2042, photodetector value 2044 for photocurrent from light detected by the optical collector, electrode stimulation pulse amplitude 2046 for the left stimulation lead, electrode stimulation pulse amplitude 2048 for the right stimulation lead, electrode stimulation pulse width 2050, and electrode stimulation pulse frequency 2052. Patient position identifier 2042 includes four positions, forward (prone)—0°, right—90°, left—270°, back (supine—180°). Each row in calibration table 2040 is associated with one of the four patient positions. Electrode stimulation pulse amplitude 2046 for the left lead can be different from electrode stimulation pulse amplitude 2048 for the right lead according to values which are derived during calibration and recorded for different spinal cord positions, corresponding to the patient position. The electrode stimulation pulse amplitude 2046 prescribes a stimulation energy to nerves in the vicinity of the left side of spinal cord. The electrode stimulation pulse amplitude 2048 prescribes a stimulation energy to nerves in the vicinity of the right side of spinal cord.

To construct table 2040, calibration methods 1600 and 1700 are performed to identify a set of right stimulator lead values for a right electrode pulse amplitude, width and frequency with a set of photocurrent levels and to identify a set of left stimulator lead values for a left electrode pulse amplitude, width and frequency with the set of photocurrent levels. The set of left stimulator lead values can be different than the set of right stimulator lead values.

In another embodiment, calibration methods 1600 and 1700 are performed where the electrode stimulation pulse amplitude for the left and right leads always have the same value.

In an alternate embodiment, calibration is performed for additional physical positions such that additional rows are placed in calibration table 1940 or calibration table 2040.

In tables 1940 and 2040, the electrode stimulation pulse width and electrode stimulation pulse frequency are shown as having constant values. However, in an alternate embodiment, the values of electrode stimulation pulse width and electrode stimulation pulse frequency are varied through a predetermined range during calibration and recorded for each patient position.

While the present invention has been described in terms of specific embodiments thereof, it will be understood in view of the present disclosure, that numerous variations upon the invention are now enabled to those skilled in the art, which variations yet reside within the scope of the present teaching. Accordingly, the invention is to be broadly construed and limited only by the scope and spirit of the claims now appended hereto.

The invention claimed is:

1. A method for stimulating a nerve location in the spinal cord comprising the steps of:
    directing an incident light beam toward the spinal cord;
    detecting the reflected light beam from the spinal cord with an optical detector;
    determining a first photocurrent level from the optical detector in response to the reflected light beam;
    determining a first current amplitude for a first electrode current from the first photocurrent level based on a calibration table stored in a memory;
    directing the first electrode current to a set of electrodes based on the first photocurrent level;
    wherein a first electric field is produced with a field strength proportional to the first electrode current to stimulate the nerve;
    determining a second photocurrent level from the optical detector;
    determining a second current amplitude for a second electrode current from the second photocurrent level based on the calibration table;
    directing the second electrode current to the set of electrodes based on the second photocurrent level;
    wherein a second electric field is produced with a field strength proportional to the second electrode current to stimulate the nerve;
    providing a controller;
    providing the memory and a processor for the controller;
    storing the calibration table in the memory;
    storing a set of historical current amplitudes; and,
    time-averaging the set of historical current amplitudes to determine the second current amplitude.

2. The method of claim 1 further comprising the steps of:
    connecting the set of electrodes to the controller;
    providing an optical emitter operatively connected to the controller;
    providing the optical detector operatively connected to the controller;
    providing at least one optical element;
    optically coupling the optical emitter and the optical detector to the at least one optical element;
    producing the incident light beam from the optical emitter;
    directing the incident light beam through the at least one optical element toward the spinal cord;
    collecting the reflected light beam from the spinal cord through the at least one optical element; and,
    receiving the reflected light beam at the optical detector.

3. The method of claim 2 including the step of optically coupling the optical emitter and the optical detector to a single optical element.

4. The method of claim 3 including the step of optically coupling the optical emitter and the optical detector to a single optical element with an optical circulator.

5. The method of claim 1 further comprising the steps of:
    deriving a set of current pulse widths for the electrode current with at least one of the steps:
        time-averaging a set of historical current pulse widths;
        time-averaging a set of current amplitudes;
        interpolating the set of current pulse widths from the calibration table.

6. The method of claim 1 further comprising the steps of:
    deriving a set of current pulse frequencies for the electrode current with at least one of the steps:
        time-averaging a set of historical current pulse frequencies;
        time-averaging a set of current amplitudes;
        interpolating the set of current pulse frequencies from the calibration table.

7. The method of claim 1 further comprising the steps of:
    providing a calibration unit, operatively connected to the controller;
    moving a patient into a set of positions;
    directing the calibration unit to generate the calibration table in response to the set of positions.

* * * * *

UNITED STATES PATENT AND TRADEMARK OFFICE
CERTIFICATE OF CORRECTION

PATENT NO. : 9,656,097 B2
APPLICATION NO. : 14/019240
DATED : May 23, 2017
INVENTOR(S) : Erich W. Wolf, II Page 1 of 1

It is certified that error appears in the above-identified patent and that said Letters Patent is hereby corrected as shown below:

Column 13; Line 1: Change "A" to -- $A_{R2}$ --

Signed and Sealed this
Eighth Day of August, 2017

Joseph Matal
*Performing the Functions and Duties of the*
*Under Secretary of Commerce for Intellectual Property and*
*Director of the United States Patent and Trademark Office*